(12) United States Patent
Glezer et al.

(10) Patent No.: US 9,354,230 B2
(45) Date of Patent: *May 31, 2016

(54) METHODS AND APPARATUS FOR CONDUCTING MULTIPLE MEASUREMENTS ON A SAMPLE

(75) Inventors: Eli N. Glezer, Chevy Chase, MD (US); Kent Johnson, Bexley, OH (US); Michael Tsionsky, Gaithersburg, MD (US); John H. Kenten, Boyds, MD (US); Jeff D. Debad, Gaithersburg, MD (US); Robert M. Umek, Silver Spring, MD (US); Paula Denney Eason, Germantown, MD (US); Hans Biebuyck, Gaithersburg, MD (US); Jacob N. Wohlstadter, Potomac, MD (US); James Wilbur, Boyds, MD (US); George Sigal, Rockville, MD (US); Niranjan Y. Sardesai, North Wales, PA (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/977,271

(22) Filed: Dec. 23, 2010

(65) Prior Publication Data
US 2011/0105354 A1    May 5, 2011

Related U.S. Application Data

(62) Division of application No. 10/238,391, filed on Sep. 10, 2002, now Pat. No. 7,858,321.

(60) Provisional application No. 60/363,498, filed on Mar. 11, 2002, provisional application No. 60/318,293, filed on Sep. 10, 2001, provisional application No. 60/318,284, filed on Sep. 10, 2001, provisional application No. 60/318,289, filed on Sep. 10, 2001.

(51) Int. Cl.
G01N 33/543    (2006.01)
C12Q 1/48    (2006.01)
G01N 33/68    (2006.01)

(52) U.S. Cl.
CPC ............ *G01N 33/5438* (2013.01); *C12Q 1/485* (2013.01); *G01N 33/54366* (2013.01);
(Continued)

(58) Field of Classification Search
CPC .................... G01N 33/5438; G01N 33/54386; G01N 33/6803; G01N 33/54366; G01N 33/54373; G01N 33/6842
See application file for complete search history.

(56) References Cited

U.S. PATENT DOCUMENTS 3,935,029 A    1/1976    Baker et al.
4,280,815 A    7/1981    Oberhardt et al.
(Continued)

FOREIGN PATENT DOCUMENTS

JP    2005-521032 A1    7/2005

OTHER PUBLICATIONS

Chen R. et al., "Simultaneous Quantification of Six Human Cytokines in a Single Sample Using Microparticle-Based Flow Cytometric Technology", *Clin. Chem.* 45(9):1693-1694 (1999).
(Continued)

*Primary Examiner* — Melanie Y Brown
(74) *Attorney, Agent, or Firm* — Scully, Scott, Murphy & Presser, P.C.

(57) ABSTRACT

Multiplexed test measurements are conducted using an assay module having a plurality of assay domains. In preferred embodiments, these measurements are conducted in assay modules having integrated electrodes with a reader apparatus adapted to receive assay modules, induce luminescence, preferably electrode induced luminescence, in the wells or assay regions of the assay modules and measure the induced luminescence.

6 Claims, 15 Drawing Sheets

(52) U.S. Cl.
CPC .... *G01N33/54373* (2013.01); *G01N 33/54386* (2013.01); *G01N 33/68* (2013.01); *G01N 33/6803* (2013.01); *G01N 33/6842* (2013.01); *G01N 33/6845* (2013.01); *Y10S 436/807* (2013.01)

(56) References Cited

U.S. PATENT DOCUMENTS

| | | | |
|---|---|---|---|
| 4,354,958 A | 10/1982 | Solomon | |
| 4,459,197 A | 7/1984 | Solomon | |
| 4,673,657 A * | 6/1987 | Christian | 436/501 |
| 4,703,017 A | 10/1987 | Campbell et al. | |
| 5,089,391 A | 2/1992 | Buechler et al. | |
| 5,093,268 A | 3/1992 | Leventis et al. | |
| 5,132,085 A * | 7/1992 | Pelanek | 422/402 |
| 5,147,806 A | 9/1992 | Kamin et al. | |
| 5,158,869 A | 10/1992 | Pouletty et al. | |
| 5,187,096 A * | 2/1993 | Giaever | G01N 33/4836 204/403.01 |
| 5,238,808 A | 8/1993 | Bard et al. | |
| 5,541,061 A | 7/1996 | Fodor et al. | |
| 5,565,325 A | 10/1996 | Blake | |
| 5,639,603 A | 6/1997 | Dower et al. | |
| 5,684,711 A | 11/1997 | Agrafiotis et al. | |
| 5,710,005 A | 1/1998 | Rittenburg | |
| 5,744,358 A | 4/1998 | Jackowski | |
| 5,807,522 A | 9/1998 | Brown et al. | |
| 5,807,755 A | 9/1998 | Ekins | |
| 5,928,918 A | 7/1999 | Offenbacher et al. | |
| 6,033,850 A | 3/2000 | Purvis | |
| 6,051,380 A * | 4/2000 | Sosnowski et al. | 435/6.11 |
| 6,110,426 A | 8/2000 | Shalon et al. | |
| 6,207,369 B1 | 3/2001 | Wohlstadter et al. | |
| 6,376,233 B1 * | 4/2002 | Wolf | B01L 3/5085 204/403.01 |
| 6,451,191 B1 * | 9/2002 | Bentsen et al. | 204/600 |
| 6,458,547 B1 | 10/2002 | Bryan et al. | |
| 6,563,581 B1 | 5/2003 | Oldham et al. | |
| 6,673,533 B1 | 1/2004 | Wohlstadter et al. | |
| 6,919,173 B2 | 7/2005 | Tsionsky et al. | |
| 2002/0190356 A1 * | 12/2002 | Buechler et al. | 257/668 |
| 2003/0039967 A1 * | 2/2003 | Kris et al. | 435/6 |
| 2003/0054571 A1 | 3/2003 | Watkins et al. | |
| 2003/0096433 A1 | 5/2003 | Meyer-Almes | |
| 2004/0022677 A1 | 2/2004 | Wohlstadter et al. | |
| 2004/0072158 A1 * | 4/2004 | Henkens et al. | 435/6 |

OTHER PUBLICATIONS

Moody M.D. et al., "Array-Based ELISAs for High-Throughput Analysis of Human Cytokines", *BioTechniques* 31(1):1186-1194 (2001).

Popovich N.D., "Mediated Electrochemical Detection of Nucleic Acids for Drug Discovery and Clinical Diagnosis", *IVD Technol.* 7(3):36-42 (2001).

Vignali D.A.A., "Multiplexed Particle-Based Flow Cytometric Assays", *J. Immunol. Methods* 243:243-255 (2000).

Walt D.R., "Bead-Based Fiber-Optic Arrays", *Science* 287(5452):451-452 (2000).

Japanese Decision of Rejection dated Dec. 17, 2014 received from Application No. 2012-019525, together with an English-language translation.

Japanese Decision of Declining Amendment dated Dec. 17, 2014 received from Application No. 2012-019525, together with an English-language translation.

* cited by examiner

Figure 8A
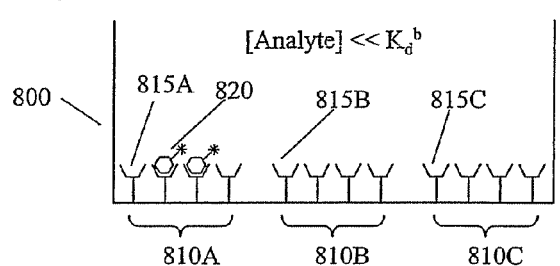
Figure 8B
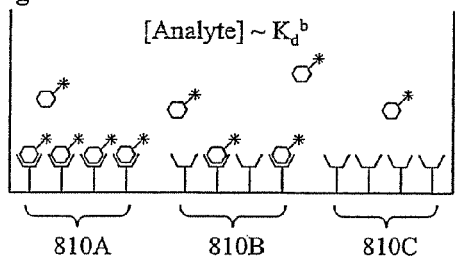
Figure 8C
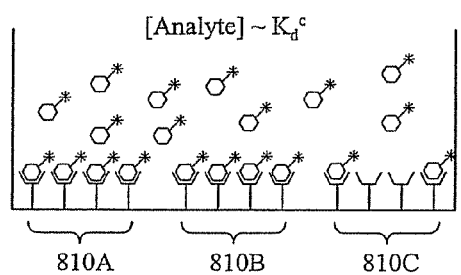
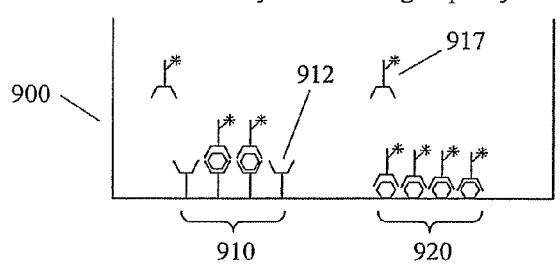
Figure 9A
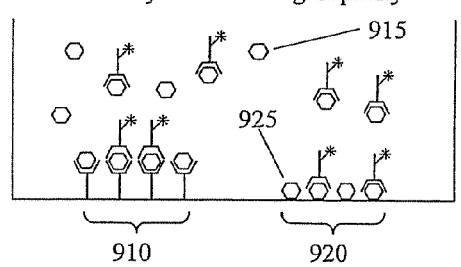
Figure 9B

Figure 15

|   | PGT | | | | |
|---|---|---|---|---|---|
|   | Enzyme / Analyte | | | | |
|   | bIgG* | SRC | ERK | SRC + ERK | SRC + ERK + bIgG* |
| B | 268 | 177 | 157 | 152 | 447 |
| CV | 13% | 8% | 4% | 6% | 11% |
| S | 1,005 | 35,696 | 1,114 | 29,508 | 29,963 |
| CV | 13% | 7% | 3% | 5% | 12% |
|   | MBP | | | | |
|   | Enzyme / Analyte | | | | |
|   | bIgG* | SRC | ERK | SRC + ERK | SRC + ERK + bIgG* |
| B | 646 | 262 | 327 | 315 | 1162 |
| CV | 4% | 6% | 11% | 16% | 8% |
| S | 1,453 | 5,955 | 11,728 | 19,062 | 22,413 |
| CV | 7% | 10% | 6% | 5% | 7% |
|   | Avidin | | | | |
|   | Enzyme / Analyte | | | | |
|   | bIgG* | SRC | ERK | SRC + ERK | SRC + ERK + bIgG* |
| B | 27,467 | 38 | 26 | 27 | 24720 |
| CV | 5% | 19% | 14% | 21% | 8% |
| S | 56,145 | 1,459 | 240 | 2,743 | 53,406 |
| CV | 4% | 16% | 13% | 20% | 4% |
|   | BSA | | | | |
|   | Enzyme / Analyte | | | | |
|   | bIgG* | SRC | ERK | SRC + ERK | SRC + ERK + bIgG* |
| B | 83 | 25 | 16 | 17 | 93 |
| CV | 13% | 22% | 20% | 19% | 21% |
| S | 162 | 94 | 139 | 338 | 553 |
| CV | 37% | 17% | 11% | 14% | 19% |

Figure 19A
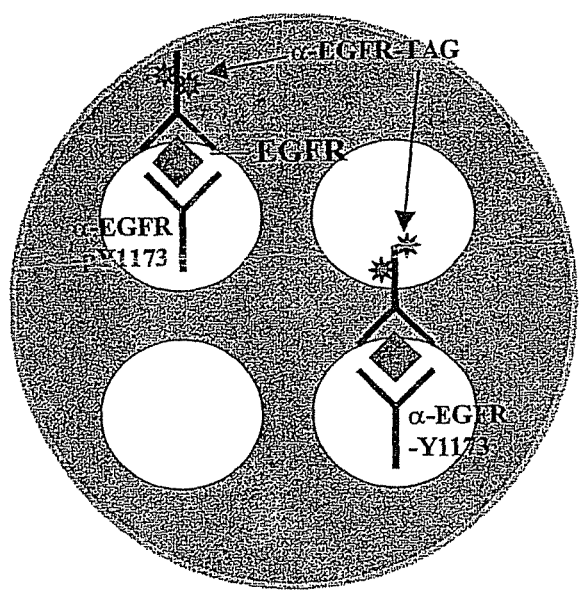
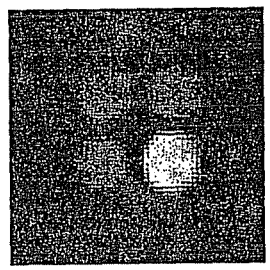
Figure 19B
0.2nM EGF
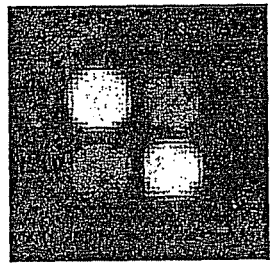
Figure 19C
5nM EGF
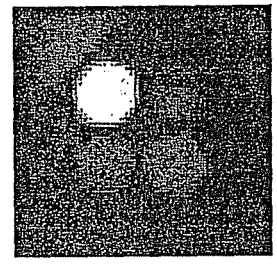
Figure 19D
200nM EGF

US 9,354,230 B2

METHODS AND APPARATUS FOR CONDUCTING MULTIPLE MEASUREMENTS ON A SAMPLE

CROSS-REFERENCE TO RELATED APPLICATIONS

The present application is a divisional of application Ser. No. 10/238,391, filed Sep. 10, 2002 now U.S. Pat. No. 7,858, 321, which claims priority to U.S. Provisional Application No. 60/363,498, filed Mar. 11, 2002; U.S. Provisional Application Ser. No. 60/318,293, filed Sep. 10, 2001; U.S. Provisional Application No. 60/318,284, filed Sep. 10, 2001; and U.S. Provisional Application Ser. No. 60/318,289, filed Sep. 10, 2001, each of which are hereby incorporated by reference.

1. FIELD OF THE INVENTION

This application relates to reagents, apparatus, systems, kits and methods for conducting multiple chemical, biochemical and/or biological assays on a sample.

2. BACKGROUND OF THE INVENTION

At this time, there are a number of commercially available instruments that utilize electrochemiluminescence (ECL) for analytical measurements including drug screening. Species that can be induced to emit ECL (ECL-active species) have been used as ECL labels. Examples of ECL labels include: i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485), oxalate, and persulfate for ECL from RuBpy and hydrogen peroxide for ECL from luminol (see, e.g., U.S. Pat. No. 5,240,863). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093, 268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369; 6,214,552 and 5,589,136 and Published PCT Nos. WO99/63347; WO00/03233; WO99/58962; WO99/32662; WO99/14599; WO98/12539; WO97/36931 and WO98/57154.

Commercially available ECL instruments have demonstrated exceptional performance. They have become widely used for reasons including their excellent sensitivity, dynamic range, precision, and tolerance of complex sample matrices. The commercially available instrumentation uses flow cell-based designs with permanent reusable flow cells. Recently, ECL instrumentation has been disclosed that uses reagents immobilized on the electrode used to induce ECL (see, e.g., U.S. Pat. Nos. 6,140,045; 6,066,448; 6,090,545; 6,207,369 and Published PCT Appl. No. WO98/12539). Multi-well plates having integrated electrodes suitable for such ECL measurements have also been recently disclosed (see, e.g., copending U.S. application Ser. Nos. 10/185,274 and 10/185, 363 (entitled "Assay Plates, Reader Systems and Methods for Luminescence Test Measurements", each filed on Jun. 28, 2002, hereby incorporated by reference). These multi-well plates having integrated electrodes include plates having multiple assay domains within a well.

The use of multi-well assay plates allows for the parallel processing and analysis of multiple samples distributed in multiple wells of a plate. Typically, samples and reagents are stored, processed and/or analyzed in multi-well assay plates (also known as microplates or microtiter plates). Multi-well assay plates can take a variety of forms, sizes and shapes. For convenience, some standards have appeared for some instrumentation used to process samples for high throughput assays. Assays carried out in standardized plate formats can take advantage of readily available equipment for storing and moving these plates as well as readily available equipment for rapidly dispensing liquids in and out of the plates. Some well established multi-well plate formats include those found on 96-well plates (12×8 array of wells), 384-well plates (24×16 array of wells) and 1536-well plate (48×32 array of well). The Society for Biomolecular Screening has published recommended microplate specifications for a variety of plate formats, the recommended specifications hereby incorporated by reference.

3. SUMMARY OF THE INVENTION

The present invention includes apparatus, systems, system components, reagents, kits and methods for performing a plurality of assays on a sample. The invention includes assay modules having one or more assay cells (e.g., wells, compartments, chambers, channels, flow cells, etc.) that comprise a plurality of assay domains (e.g., discrete locations on a module surface where an assay reaction occurs and/or where an assay signal is emitted for carrying out a plurality of assay measurements. The assay cell is, preferably, adapted to hold a volume of fluid in contact with assay domains within the assay cell without contacting assay domains in other assay cells of an assay module. In preferred embodiments, the assay modules are multi-well plates, the plates comprising a plurality of wells, one or more of the wells comprising a plurality of assay domains (referred to herein as Multi-Domain Multi-Well Plates or MDMW Plates). Preferably, the plates are designed to be compatible with plate handling equipment (e.g., fluid dispensers, plate washers, plate stackers, plate movers, and/or plate readers) designed for use with standard format multi-well plates.

The assays of the invention are preferably coupled to a detection step that involves the use of an electrode, the generation of light, and the measurement of the generated light. Examples of processes that may be used in such a detection step include electrochemiluminescence (also referred to as electrogenerated chemiluminescence), electroluminescence, and chemiluminescence triggered by an electrochemically-generated species. For the purposes of the application and for convenience, these three processes will be referred to as "electrode induced luminescence". Electrochemiluminescence involves electrogenerated species and the emission of light. For example, electrochemiluminescence may involve luminescence generated by a process in which one or more reactants are generated electrochemically and undergo one or more chemical reactions to produce species that emits light, preferably repeatedly. The invention also relates to assays and measurements that do not require the use of an electrode, for example, the assays of the invention may be based on measurements of chemiluminescence, fluorescence, bioluminescence, phosphorescence, optical density and processes that involve the emission of light from a scintillant. The invention also relates to assays and measurements that do not involve luminescence, for example, the assays of the invention may be based on measurements of electrochemical processes (e.g., processes involving the measurement or generation of current or voltage), electrical processes (e.g., processes involving the measurement of resistance or impedance), surface plasmon resonance or optical interference effects.

Accordingly, in certain preferred embodiments of the invention, the assay modules and/or MDMW Plates are adapted to allow assay measurements to be conducted using electrode induced luminescence measurements (most preferably, electrochemiluminescence measurements), e.g., as described in copending U.S. application Ser. Nos. 10/185,274 and 10/185,363 (entitled "Assay Plates, Reader Systems and Methods for Luminescence Test Measurements"), each filed on Jun. 28, 2002, hereby incorporated by reference. Advantageously, assay domains patterned on a surface of a well (e.g., on an electrode in a well adapted for conducting electrode induced luminescence measurements) are defined by physical boundaries which can include ledges or depressions in the surface, patterned materials deposited or printed on the surface, and or interfaces between regions of the surface that vary in a physical property (e.g., wettability). Such physical boundaries simplify the patterning of reagents on surfaces of a well by confining and preventing the spreading of small drops of reagents applied to an assay domain.

By providing two levels of multiplexing (multiple wells per plate and multiple domains per well), MDMW Plates provide a variety of advantages over conventional multi-well plates that only have one assay domain per well. For example, a MDMW Plate having N wells and M assay domains per well allows a panel of M assays to be run on a plurality of N samples. Conducting the same series of assays on conventional N-well plates would require M plates, M times more sample and reagents, and considerably more pipetting and plate handling steps to achieve the same performance. Conducting the same series of assays on conventional array "chips" would involve the handling and movement of N chips and would likely not be compatible with standard plate handling equipment designed for use with multi-well plates. Conducting the same series of assays on a single ultra-high density multi-well plate with M×N wells would generally lead to reduced assay sensitivity (sample volume and, therefore, number of analyte molecules, tends to scale inversely with the density of wells on a plate) as well as to other problems associated with ultra-high density plate formats (e.g., expensive and complicated fluid dispensing equipment, lack of mixing, evaporative losses, trapping of air bubbles, inability to carry out wash steps, etc.).

The invention includes assay formats that take advantage of multiplexing available through the use of assay cells comprising multiple assay domains and, in particular, through the use of MDMW Plates. Some examples of preferred assay formats are described below. It is understood that while some of the forms are described in terms of MDMW Plates, they can be applied to other assay modules comprising assay cells with multiple domains. It is also understood that the multiplicity of assay domains available within an assay cell allows many of the formats described below to be combined within one cell.

In one preferred assay format, a plurality of analytes or activities are measured within one well of a MDMW plate. For example, panels of assays may be developed for measuring a plurality of analytes or activities associated with a particular biological system (e.g., panels of immunoassays or hybridization assays for monitoring cytokine mRNA or protein levels), disease state (e.g., panels of assays for cardiac markers, for identifying allergens responsible for allergic reactions, for identifying infectious organisms, etc.), tissue type, organism, class of protein, enzyme or biological molecule, etc. In one embodiment, a panel of assays is used to provide a fingerprint for identifying a biological system (e.g., a pattern of analyte levels associated with a particular cell type, organelle type, organism type, tissue type, bacteria or virus). For example, a plurality of assays for different components found within a genus of biological systems can be used to identify species or subspecies within that genus. In another embodiment, a differential measurement involving a plurality of assays for different components within a biological system is used to identify the state of the biological system (e.g., diseased vs. normal state, activated vs. normal state, etc.) or to identify the components within a biological system that are affected by an external condition or stimulus (e.g., changes in the distribution of components associated with development of a disease state, addition of a stimulatory species, addition of a potential drug candidate, changes in environmental conditions such as pH, temperature, etc.). Assay panels may also be used to determine the function of one or more proteins. For example, a protein may be screened against a patterned library of enzyme substrates and/or potential binding partners to identify enzymatic or binding activities. Conversely, a patterned library of proteins may be exposed to a known biological material to determine if any of the proteins binds to, reacts with or is otherwise transformed by the biological material.

In another preferred assay format, some fraction of the assay domains present in a well are devoted to internal standards, controls or calibrators. For example, one or more assay domains may be left uncoated or may be coated with a blocking agent or a biomaterial not expected to participate in a reaction with a sample; such assay domains may be used to measure and/or correct for non-specific binding of labels to surface in the well. In another example, one or more assay domains is coated with a labeled reagent (e.g., a reagent labeled with an ECL label); such assay domains may be used to measure and/or correct for conditions that may affect the generation and measurement of signal (e.g., ECL) from a label (e.g., pH, temperature, chemical interferents, colored species, etc.). In another example, one or more assay domains are used to carry out a control assay for a control analyte that is spiked into the assay mixture. Preferably, the control assay is similar in format to assays carried out on other assay domains. Control assays may be used to measure and/or correct for non-specific binding, conditions that affect the generation of signal from a label and conditions that affect assay reactions (variations in incubation time, temperature, mixing, etc.).

In another preferred assay format the same analyte or activity is measured in multiple domains within a well; such redundancy can allow for greater statistical confidence in an assay result. Such multiple measurements of the same analyte may involve the use of multiple roughly identical assay domains or, alternatively, may involve the use of assay domains that vary in some property (for example, domain size, domain location, surface density of an assay reagent, blocking agent, assay reagent affinity, assay reagent specificity, assay format, sensitivity to interferents, sensitivity to temperature, assay kinetics, sensitivity to optical distortion, etc.) so as to account for, detect, and/or compensate for a source of assay error (e.g., inconsistent or non-homogenous mixing, steric crowding of assay reagents in an assay domain, non-specific binding, matrix effects, interfering species, imprecise temperature control, imprecise timing of assay steps, exceeding of assay dynamic range, variation in fluid volume or meniscus shape, etc.).

In another preferred assay format, the same analyte or activity is measured in multiple domains within a well, the domains being comprised on individually addressable electrodes. In such a system one may measure the kinetics of an assay reaction by sequentially applying electrical energy to individual assay domains at selected times and measuring the change in electrical current, electrical potential, or, preferably, electrode induced luminescence (most preferably, ECL) over time. By measuring different time points at different assay domains, it is not necessary to repeatedly apply possibly damaging electrical energy to the same assay domain.

In another preferred assay format, the same analyte is measured at different assay domains within a well, the different assay domains being designed to measure a different property or activity of the analyte. In one embodiment, an enzyme with multiple different activities is measured in a well comprising different assay domains that differ in their selectivity for each enzymatic activity of the enzyme (e.g., assay domains that comprise substrates for selected enzymatic activities and/or assay domains that are capable of capturing and measuring the substrates or products of selected enzymatic activity), that are designed to measure binding activities of the enzyme (e.g., assay domains comprising potential binding partners of the enzyme or that are designed to capture the enzyme so as to allow the measurement of interaction with potential binding partners in solution) and/or assay domains designed to measure the ability of the enzyme to act as a substrate for a second enzyme (e.g., binding domains designed to allow for a specific binding assay of the product of the action of the second enzyme on the first enzyme). In another embodiment, a well comprises a domain for measuring the amount of an enzyme (e.g., via a binding assay such as an immunoassay) and one or more other domains for measuring one or more activities associated with the enzyme; this embodiment allows the measured activity to be referenced to the amount of enzyme. The inclusion of assay domains capable of capturing an enzyme of interest has the added advantage of allowing the purification of the enzyme from a crude sample within the assay well. In yet another embodiment of the invention, a well comprises an assay domain capable of capturing an enzyme of interest and one or more additional assay domains for measuring an activity of the enzyme of interest. Methods using such a well may include a wash step for purifying the enzyme from impurities in a crude enzyme preparation.

In another preferred assay format, the number of measurements that can be carried out in one well is increased by co-immobilizing a plurality of assay reagents in each domain within the well. For example, one can screen for the binding partner of a biomaterial of interest by patterning a library of M potential binding partners on M assay domains in a well, exposing the well to a sample containing a labeled biomaterial and looking for the assay domain that produces a signal indicative of a binding event. Alternatively, one can pattern a library of M×I potential binding partners by co-immobilizing I potential binding partners in each assay domain. A signal at a specific assay domain would indicate that one of I potential binding partners has binding activity; the identity of the binding partner could be determined by then individually testing each component of that assay domain. Advantageously, an assay kit may contain a first MDMW plate that multiplexes assay reagents within assay domains of a well and a set of additional MDMW plates that are patterned so as to allow the testing of each individual component of an assay domain in the first plate (e.g., a second MDMW Plate having a well with a plurality of assay domains each comprising one component of an assay domain on the first plate).

In another preferred embodiment, the number of assay components that can be patterned and uniquely identified on an array of M domains (where M is an integer greater than three) is increased by patterning each reagent into a unique group of assay domains. For example, one can pattern a library of up to $Z=(M!)/[2!(M-2)!]$ potential binding partners (preferably, >M binding partners) so that up to $(M-1)$ binding partners are immobilized in each domain but one or more (preferably, all) binding partners are immobilized in a unique pair of domains (the other binding partners, preferably, being immobilized in unique sets of one domain. In this case, those one or more binding partners can be identified by looking for pairs of assay domains producing signals indicative of a binding event. By way of example, wells comprising 4, 7, 10, and 25 assay domains have, respectively, 6, 21, 45 and 300 unique pairs of domains per well. Similarly, one can pattern a library of up to $(M!)/[Z!(M-Z)!]$ potential binding partners (preferably, >M binding partners) so that one or more (preferably, all) binding partners are immobilized in a unique group of Z domains. The number of components that can be screened in a given well can be further increased by patterning some components in groups of $Z_1$ domains, others in groups of $Z_2$ domains and so on, where $Z_1, Z_2, \ldots$ are integers greater than or equal to one and less than or equal to M.

In another preferred assay format, potentially cross-reacting analytes are measured in different domains in the same well. For example, two similar analytes (a first analyte and a second analyte) may be measured using two assay domains comprising binding reagents (a first domain selective for the first analyte and a second domain selective for the second analyte) even if the binding reagents are only partially selective for each analyte. By carrying out the assays in the same well, the binding of the second analyte to the second domain reduces its effective concentration in solution and reduces its ability to interfere with the measurement of the first analyte at the first domain. To the extent that such effects do not completely eliminate cross-reactions, the ability to measure both cross-reacting species allows for the mathematical deconvolution of signals so as to further reduce the effect of cross-reactions on assay results. Such deconvolutions can, e.g., be based on empirical calibrations (e.g., using a two dimensional matrix of calibrators varying the concentrations of both analytes, preferably the calibrators are chosen and the results modeled using Design of Experiment techniques) or on theoretical models (e.g., models derived using the thermodynamic and/or kinetic parameters associated with each possible binding interaction). Optionally, only the first analyte is measured and the second domain serves only to sequester the second analyte and prevent it from interfering with the measurement of the first analyte. The methods described above for reducing cross-reactions and interferences can be used to i) reduce and/or account for interfering substances in crude biological samples (e.g., blood, plasma, serum, tissue extracts, cell extracts) such as bilirubin, lipid, hemoglobin and/or ii) to aid in preventing and/or to prevent assay interference and cross-reactions from closely related species, e.g., to aid in measuring and distinguishing between closely related drugs and related metabolites, steroidal hormones and related metabolites, vitamins and related metabolites, modified forms of proteins, nucleic acids and saccharides (e.g., different phosphorylation states of an analyte, between different degradation states of an analyte, different bound states of an analyte, etc.), etc.

In another preferred assay format, a plurality of different assay domains in a well are adapted to measure different forms of an analyte of interest. By way of example, domains may be adapted to measure free and bound forms of an analyte of interest (e.g., free PSA vs. bound PSA), to measure unmodified and/or modified forms of an analyte of interest (examples of modifications that can be measured include, but are not limited to, phosphorylation, ubiquitination, prenylation, myristoylation, glycosidation), and/or to measure cleavage or degradation products of an analyte (e.g., protease, nuclease or glycosidase products). Alternatively, one assay domain generically measures the total amount of multiple forms of an analyte and a second assay domain is specific for one form of the analyte (e.g., for measuring free PSA vs. total PSA).

In another preferred assay format, the starting material/substrate and product (and, optionally, intermediates and/or side products) in a reaction of interest are measured at different assay domains of a well of a MDMW Plate. In one embodiment, measurements in different wells are carried out for different reaction times, allowing for a complete kinetic characterization of the reaction. In a second embodiment, assays for the starting material and product (or any two species produced and/or consumed in the reaction) show some level of cross-reactivity; as described above, measurement of both species can be used to reduce the effect of the cross-reactivity. In a third embodiment, measurement of both starting material and product allows one to correct for variations in the original amount of the starting material. Such corrections are especially important when following reactions or activities in complex biological systems such as cells or tissue. For example, in following the phosphorylation of a cellular receptor in response to activation of the cell, it is desirable to correct the measured amount of phosphorylated receptor to account for variations in the level of receptor protein expression in the cell line. Measurement of phosphorylated and nonphosphorylated forms of the receptor allows the extent of phosphorylation to be expressed as a percentage. Alternatively, the same information can be obtained through measurements of total receptor and phosphorylated receptor.

In another preferred assay format, a well comprises a first assay domain containing a labeled substrate for a cleavage reaction and a second assay domain containing a binding reagent capable of capturing the product of the cleavage reaction. Preferably, the substrate is linked to a label (preferably an ECL label) such that the cleavage reaction results in the release, from the first assay domain of a cleavage product linked to the label. The extent of the cleavage reaction may be followed by measuring the drop of signal from the first assay domain and the increase in signal from the second assay domain. By way of example, the binding reagent may be an antibody (e.g., an antibody specific for a peptide released by proteolytic activity) or a nucleic acid probe (e.g., a probe specific against an oligonucleotide released by a nuclease activity) directed against the cleavage product. Alternatively, the substrate may be further linked to a capture moiety (e.g., a hapten or biotin) such that the released cleavage product comprises both a label and a capture moiety. In this alternate embodiment, the binding reagent can be a binding reagent directed against the capture moiety (e.g., an antibody directed against the hapten, avidin, or streptavidin).

In another preferred assay format, a library of enzymes is co-immobilized with binding reagents capable of capturing enzyme products so as to form an array of assay domains having assay domains that contain both an enzyme and a binding reagent capable of capturing a product of the enzyme. Such an array allows the signals derived from the enzyme reactions to be produced in a pattern that corresponds to the arrangement of enzymes. In one embodiment, the enzymes are paired with binding reagents that are preferentially specific for the product of that enzyme. In another embodiment, the binding reagents are capable of binding the products of a plurality of enzymes in the well. In such a case, the assay domains are spaced appropriately and carried out under appropriate conditions (e.g., in the absence of mixing) to increase the probability that a product produced in one domain will bind binding reagents in that same domain before it has the opportunity to diffuse to a different domain. For example, a library of tyrosine kinases may be patterned into an array of assay domains, each domain also comprising an anti-phosphotyrosine antibody. Introduction of one or more tyrosine kinase substrates (preferably, linked to a label, most preferably, linked to an ECL label) leads to phosphorylation of the substrates and capture of the labeled product by the anti-phosphotyrosine antibody. The labeled product produced in a domain will be preferentially captured by antibodies in the same domain, ensuring that the signal generated in a domain is representative of the activity of the enzyme in that domain.

In another preferred assay format, multiple assay domains are used to aid in screening antibodies (or other binding reagents) for a binding reagent with a desired specificity for a binding species. Samples (e.g., supernatants from hybridoma cultures) are contacted with a plurality of assay domains. One assay domain comprises the binding species. The others include controls for specificity and cross-reactivity (e.g., closely related substances, potential assay interferents, a carrier protein used in an immunization procedure used to generate the binding reagents, linkers used in generating carrier protein-hapten conjugates, etc.). In one embodiment, the binding of a binding reagent can be detected using a labeled secondary binding reagent that broadly binds a class of binding reagents (e.g., an anti-species antibody). In another embodiment, a plurality of binding domains comprise a panel of anti-species antibodies directed against different antibody classes (alternatively, any antibody class specific binding reagent may be used) and the binding domains are contacted with a hybridoma supernatant (or other sample containing antibodies) in order to determine the class of the antibody in the supernatant. In one preferred embodiment, the binding of binding reagents to specific domains is detected using a labeled secondary binding reagent that broadly binds a class of binding reagents (e.g., an anti-species antibody) so as to measure the amount of all antibodies in the sample. Alternatively, a labeled hapten may be used as the detection reagent so that only the class of antibodies having a desired specificity is determined.

In another preferred assay format, multiple assay domains are used to expand the dynamic range of an assay beyond what can be achieved using a single assay domain. For example, a binding assay may involve the use of a plurality of binding domains comprising binding reagents that differ in their affinity for the analyte of interest. The domain with the highest affinity binding reagent is used to measure low concentrations of analyte. Domains with intermediate or weak affinity binding reagents are used for samples having intermediate or high concentrations of analyte. In the case of assay domains with intermediate or weak affinity binding reagents, the binding reagents are, preferably, selected to have dissociation constants roughly centered in the range of analyte concentrations to be measured by that assay domain.

In the specific case of sandwich binding assays that experience a hook effect at high concentrations, the dynamic range of the assay may be expanded by pairing the sandwich immunoassay (conducted in a first assay domain) with a competitive assay for the same analyte (conducted in a second assay domain). Preferably, the competitive assay involves the competition of analyte in a sample with an immobilized analog of the analyte for binding to a labeled anti-analyte antibody. More preferably, the analog of the analyte does not comprise the epitope recognized by the capture antibody in the sandwich assay (e.g., the analog of the analyte may be a peptide fragment derived from a protein analyte that does not include the epitope recognized by the capture antibody). The sandwich and competitive assays may use the same labeled detection antibody. Advantageously, the amount of detection antibody is roughly equal to the sum of the amount of analog of the analyte and capture antibody. For amounts of analyte lower than the amount of capture antibody, the sandwich assay will give a signal roughly linearly dependent on the concentration of analyte and the competitive assay will be roughly independent of analyte concentration. Amounts of analyte higher than the amount of capture antibody will lead to decreases is signal from both the sandwich assay (due to hook effect, i.e., the increase in the probability that the analyte will be bound to only one of the detection or capture antibody and not both at the same time) and the competitive assay (due to competition). In this region, the competitive assay may be used to quantify analyte or to simply warn that the dynamic range of the sandwich assay has been exceeded. In an alternate embodiment, capture reagents are chosen that differ in binding kinetics; the binding time and kinetic constants are chosen so that i) low concentrations of analyte are measured in fast binding assay domains and ii) high concentrations of analyte (exceeding the binding capacity of the assay domains) are measured in kinetically controlled binding reactions at slow binding domains.

In another preferred assay format, one or more assay domains in a well are used for purposes other than as a solid phase for a solid phase assay. By way of example: i) an assay domain may comprise binding reagents for sequestering an assay interferent; ii) an assay domain may comprise binding reagents for capturing and purifying a biological material (e.g., a protein of unknown function, an enzyme, an enzyme substrate, a binding partner in a binding reaction, etc.) from a crude preparation such as blood, serum, cell lysates, tissue samples, etc. and/or iii) an assay domain may be used as a location for storing dried reagents to be rehydrated and dissolved during the course of an assay (e.g., binding reagents, enzymes, enzyme substrates, controls, calibrators, buffers, blocking agents, detergents, labeled-reagents, ECL coreactants, inhibitors, drug candidates, etc.). Preferably, the dried reagents in one assay domain are prevented, during preparation and storage of an assay well, from contacting the other assay domains in a well so as to prevent unwanted interactions between reagents. In such case, the dried reagents do not contact other assay domains until sufficient sample volume is added to the well to spread the sample across all the domains. Advantageously, when storing dried reagents in an assay domain, the assay domain is surrounded by a physical boundary (e.g., ledges or depressions on a surface of the well, patterned materials deposited or printed on the surface, and or interfaces between regions of the surface that vary in a physical property such as wettability) that allows small drops of fluids to be confined on the assay domain but also allows a larger volume of fluid to spread over multiple domains. In one embodiment of a competitive binding assay, one assay domain of a well comprises an immobilized binding reagent and another assay domain comprises a dried labeled competitor; this arrangement prevents the competitor from binding to the binding reagent prior to the addition of sample. In one embodiment of a sandwich binding assay, a first assay domain of a well comprises an immobilized capture binding reagent and a second assay domain comprises a dried labeled binding reagent; this arrangement prevents the labeled binding reagent from binding non-specifically to the first assay domain, e.g., during drying or storage of the reagents. In one embodiment of an enzyme inhibition assay, a first assay domain of a well comprises an enzyme substrate (dried on or immobilized in the assay domain) and a second assay domain comprises a dried enzyme; this arrangement prevents the enzyme from acting on the substrate prior to the addition of the sample containing an inhibitor.

The invention includes assay modules and MDMW Plates adapted to carry out assays using one or more assay formats of the invention, methods of using the modules or plates, methods of making the modules or plates, kits including the plates and one or more reagents used in an assay, and systems including plates and apparatuses for reading plates. The invention includes the measurement of analytes or chemical, biological or biochemical activities using the modules, plates or methods of the invention. The invention also includes the measurement or identification (e.g., in a screen of a library of potential drugs) of modulators (e.g., inhibitors or enhancers) of such chemical, biological or biochemical activities. The invention also includes the application of the plates, modules or methods of the invention to the characterization of a protein. For example a protein may be screened against a library of biological materials to identify biological materials that bind the protein, accept the protein as an enzymatic substrate, are modified by an enzymatic activity of the protein, or otherwise interact with the protein. Conversely, a biological material may be screened against a library of proteins to identify the proteins that bind the biological material, accept the biological material as an enzymatic substrate, are modified by an activity of the biological material, or otherwise interact with the biological material.

4. DESCRIPTION OF THE FIGURES

FIGS. 8A-8C are schematic representations of expanded dynamic range binding assays, according to preferred embodiments of the invention, comprising three assay domains of varying affinity for the analyte.

FIGS. 9A-9B are schematic representations of expanded dynamic range binding assays, according to preferred embodiments of the invention, comprising a sandwich binding assay and a competitive binding assay for the same analyte.

FIG. 15 is a table showing the selectivity of a MDMW Plate designed to measure two different kinase activities.

Figure 16:
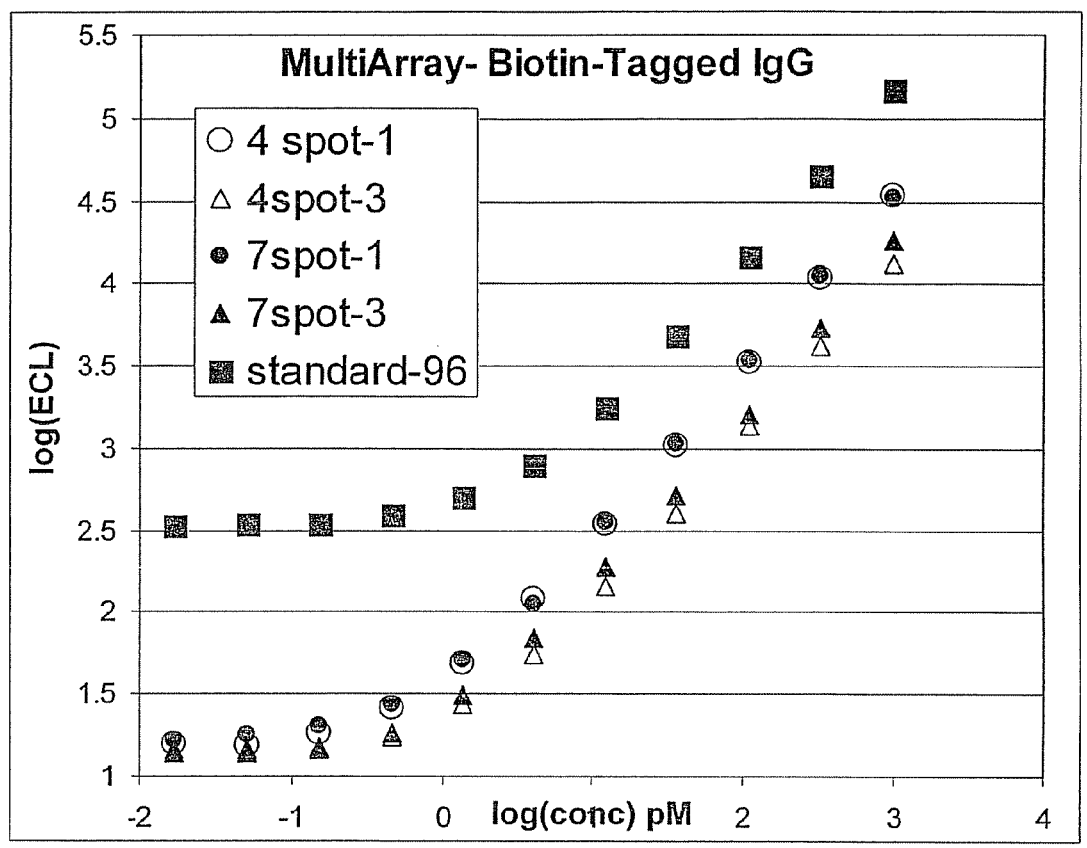
Figure 17A:
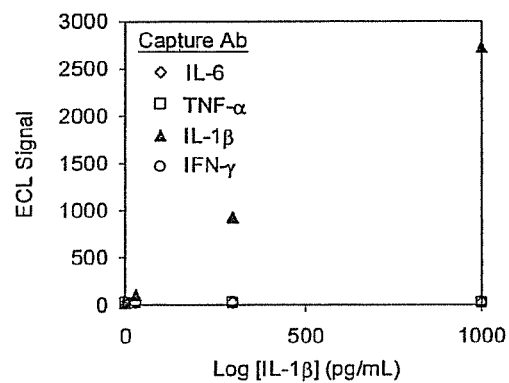
Figure 17B:
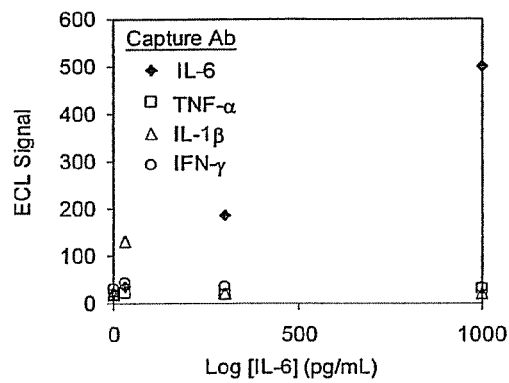
Figure 17C:
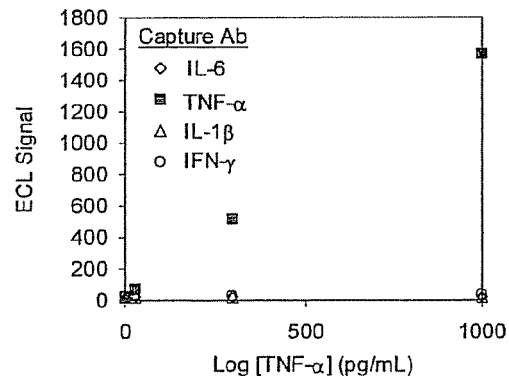
Figure 17D:
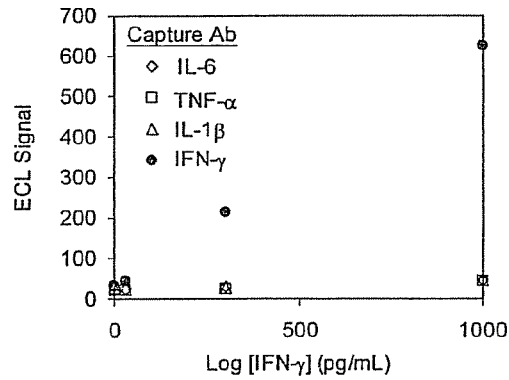

FIG. 16 plots signal as a function of the concentration of bovine IgG that is labeled with biotin and a sulfonated derivative of Ru(bpy)$_3$. Data is plotted for MDMW Plates having avidin-coated assay domains that vary in number and size.

FIGS. 17A-17D demonstrate the independent measurement by ECL sandwich immunoassay of four analytes (IL-1β, IL-6, TNF-α and IFN-γ) in wells of a multi-well assay plate. The working electrode in each well is patterned with four assay domains, each assay domain comprising a capture antibody specific for one of the analytes. The plots show the ECL signal emitted from each assay domain as a function of the concentration of each analyte.

Figure 18:
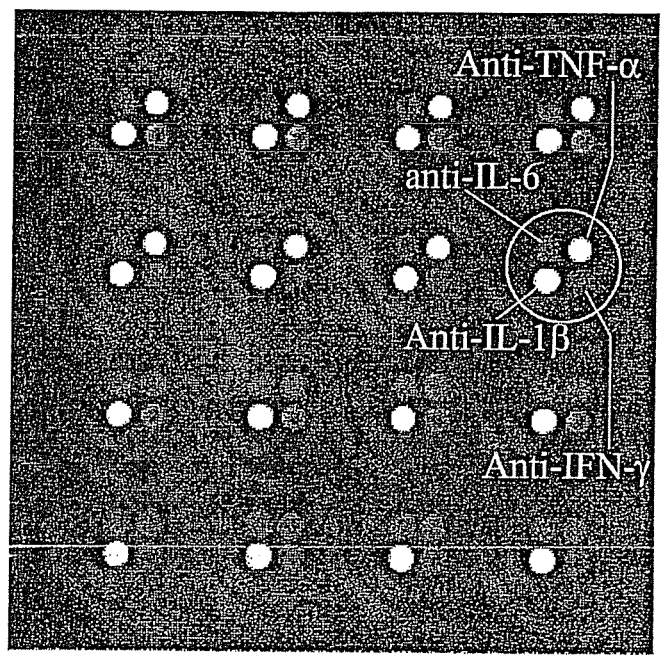

FIG. 18 is a CCD camera image showing the independent measurement by ECL sandwich immunoassay of four analytes (IL-1β, IL-6, TNF-α and IFN-γ) in wells of a multi-well assay plate. The working electrode in each well is patterned with four assay domains, each assay domain comprising a capture antibody specific for one of the analytes. The figure shows an image of the ECL emitted from a sector of wells used to assay samples containing varying mixtures of the four analytes. The highlighted well is annotated to show the arrangement of the four assay domains. That specific well was used to assay a sample having 250 pg/mL each of IL-1β and TNF-α and 8 pg/mL each of IL-6 and IFN-γ.

FIG. 19A is a schematical representation of a 4-spot well adapted for an assay for EGF induced Receptor Autophosphorylation at Tyrosine 1173 using MSD™ Standard 4-spot MULTI-ARRAY® Plates according to one embodiment of the invention. FIGS. 19B-19D are CCD images of wells of the plate having different concentrations of EGF.

5. DETAILED DESCRIPTION OF THE INVENTION

The assay domains of the invention may be adapted to carry out assays in a wide range of formats. Preferably, assay measurements are coupled to the capture or release of detectable label (e.g., an enzyme, particle, photoluminescent species, chemiluminescent species, electrochemiluminescent species, electroactive species, radioactive species, magnetic species, etc.) from a solid phase, preferably, a surface of an assay domain. Preferably, the label is detectable by electrode induced luminescence (most preferably, electrochemiluminescence) and the solid phase is an electrode adapted to induce electrode induced luminescence (preferably, electrochemiluminescence). By analogy, the assay concepts described herein can also be applied to solid phase assay formats that do not require the use of a label such as surface plasmon resonance and optical interference techniques.

Figure 1A:
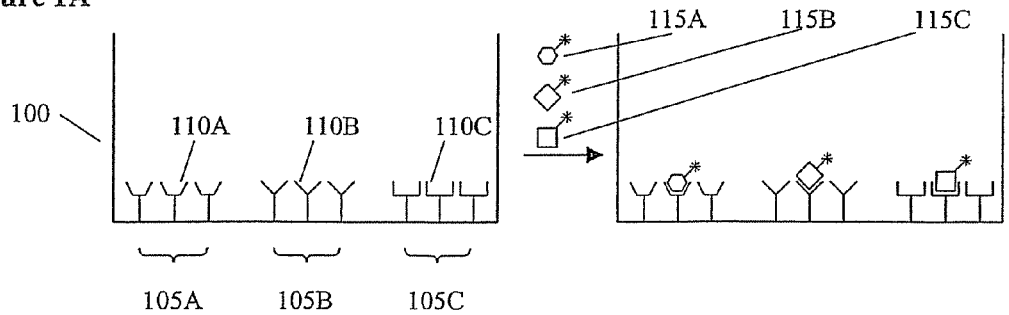
FIG. 1A is a schematic representation, according to one embodiment of the invention, of a panel of binding assays.

FIGS. 1A-1D are schematic representations that show selected examples of assay panels that may be carried out in assay cells (preferably, wells of a MDMW Plate) comprising multiple assay domains. FIG. 1A illustrates a panel of binding assays carried out in a well 100 of a MDMW Plate having assay domains 105A-C, comprising immobilized binding reagents 110A-C directed against labeled analytes 115A-C. Suitable binding reagent/analyte pairs are known in the art and include antibody/hapten, antibody/antigen, receptor/ligand, nucleic acid sequence/complementary sequence, lectin/sugar, nucleic acid/nucleic acid binding protein, protein/protein (e.g., proteins that dimerize, aggregate form binding complexes), etc.

Figure 1B:
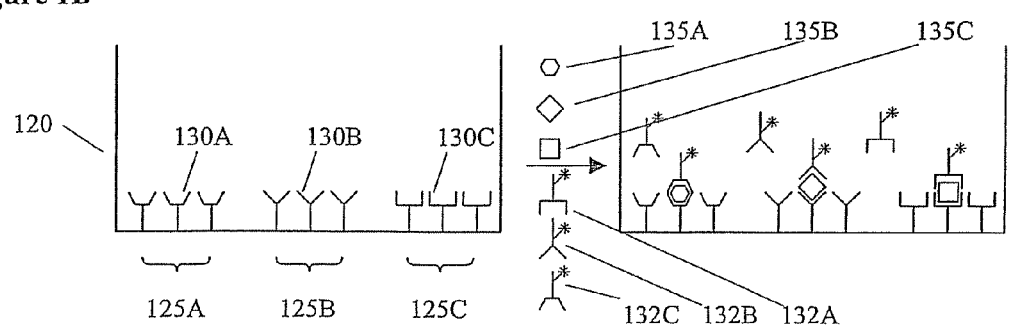
FIG. 1B is a schematic representation, according to one embodiment of the invention, of a panel of sandwich binding assays.

FIG. 1B illustrates a panel of sandwich binding assays carried out in a well 120 of a MDMW Plate having assay domains 125A-C comprising immobilized capture binding reagents 130A-C and soluble detection binding reagents 132A-C directed against analytes 135A-C. In one preferred embodiment, the panel is a panel of sandwich immunoassays. In another preferred embodiment, the panel is a panel of sandwich nucleic acid hybridization assays.

Figure 1C:
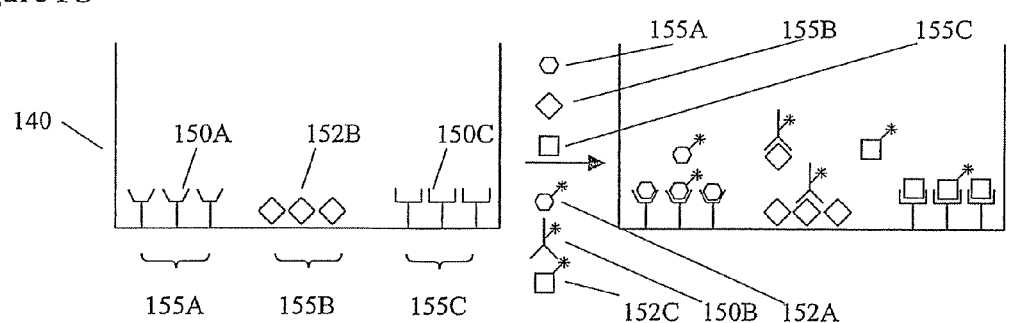
FIG. 1C is a schematic representation, according to one embodiment of the invention, of a panel of competitive binding assays.

FIG. 1C illustrates a panel of competitive binding assays carried out in a well 140 of a MDMW Plate having assay domains 145A-C. Analytes 155A-C compete with competitors 152A-C for binding to binding reagents 150A-C. If the competitor of an analyte is labeled, the corresponding binding reagent is immobilized, or visa versa. In one preferred embodiment, the panel is a panel of competitive immunoassays.

Figure 1D:
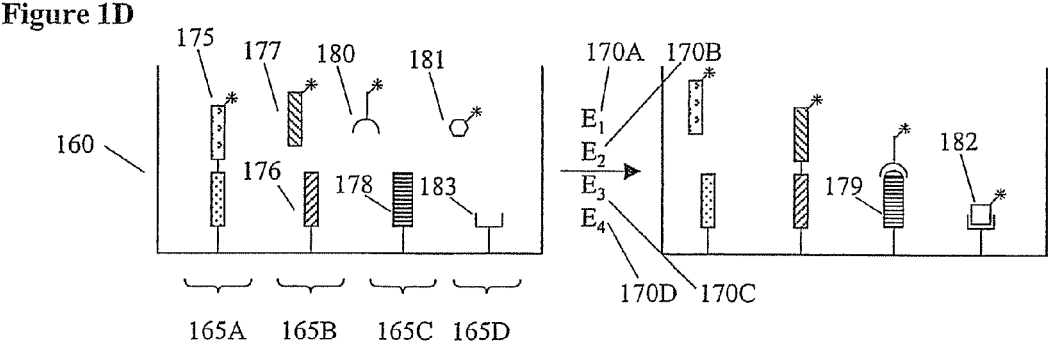
FIG. 1D is a schematic representation, according to one embodiment of the invention, of a panel of enzyme assays.

FIG. 1D illustrates a panel of enzyme assays carried out in well 160 of a MDMW Plate. Enzyme 170A cleaves labeled substrate 175 (immobilized in assay domain 165A) to release a labeled product from the assay domain. Enzyme 170B joins substrate 176 (immobilized in assay domain 165B) and labeled substrate 177 to link the label to the assay domain. Enzyme 170C modifies substrate 178 (immobilized in assay domain 165C) to make a product 179 that is recognized by labeled binding reagent 180. Enzyme 170D catalyzes the conversion of labeled substrate 181 to labeled product 182.

Labeled product 182 is then captured by binding reagent 183 (immobilized in assay domain 165D). In an alternate embodiment, the label is omitted from substrate 181 and product 182 and product 182 is detected by addition of a labeled detection binding reagent to form a sandwich complex. Enzymes (and other chemical, biochemical, and/or biological activities) that can be measured by one or all of the formats described in FIG. 1D include, but are not limited to, nucleic acid polymerases, nucleic acid ligases, helicases, integrases, nucleases, proteases, protein synthesis, glycosidases, phosphatases, kinases, prenylation enzymes, myristoylation enzymes, etc.

Useful panels include panels of assays for analytes or activities associated with a specific biochemical system, biochemical pathway, tissue, organism, cell type, organelle, disease state, class of receptors, class of enzymes, etc. Preferred panels include immunoassay for cytokines and/or their receptors (e.g., one or more of TNF-α, TNF-β, IL1-α, IL1-β, IL2, IL4, IL6, IL10, IL12, IFN-γ, etc.), growth factors and/or their receptors (e.g., one or more of EGF, VGF, TGF, VEGF, etc.), second messengers (e.g., cAMP, cGMP, phosphorylated forms of inositol and phosphatidyl inositol, etc.) drugs of abuse, therapeutic drugs, auto-antibodies (e.g., one or more antibodies directed against the Sm, RNP, SS-A, SS-B Jo-1, and Scl-70 antigens), allergen specific antibodies, tumor markers, cardiac markers (e.g., one or more of Troponin T, Troponin I, myoglobin, CKMB, etc.), markers associated with hemostasis (e.g., one or more of Fibrin monomer, D-dimer, thrombin-antithrombin complex, prothrombin fragments 1 & 2, anti-Factor Xa, etc.), markers of acute viral hepatitis infection (e.g., one or more of IgM antibody to hepatitis A virus, IgM antibody to hepatitis B core antigen, hepatitis B surface antigen, antibody to hepatitis C virus, etc.), markers of Alzheimers Disease (β-amyloid, tau-protein, etc.), markers of osteoporosis (e.g., one or more of cross-linked N or C-telopeptides, total deoxypyridinoline, free deoxypyridinoline, osteocalcin, alkaline phosphatase, C-terminal propeptide of type I collagen, bone-specific alkaline phosphatase, etc.), markers of fertility (e.g., one or more of Estradiol, progesterone, follicle stimulating hormone (FSH), luetenizing hormone (LH), prolactin, β-hCG, testosterone, etc.), markers of congestive heart failure (e.g., one or more of β-natriuretic protein (BNP), a-natriuretic protein (ANP), endothelin, aldosterone, etc.), markers of thyroid disorders (e.g., one or more of thyroid stimulating hormone (TSH), Total T3, Free T3, Total T4, Free T4, and reverse T3), and markers of prostrate cancer (e.g., one or more of total PSA, free PSA, complexed PSA, prostatic acid phosphatase, creatine kinase, etc.). Preferred panels also include nucleic acid arrays for measuring mRNA levels of mRNA coding for cytokines, growth factors, components of the apoptosis pathway, expression of the P450 enzymes, expression of tumor related genes, etc. Preferred panels also include nucleic acid arrays for genotyping individuals (e.g., SNP analysis), pathogens, tumor cells, etc. Preferred panels also include libraries of enzymes and/or enzyme substrates (e.g., substrates and/or enzymes associated with ubiquitination, protease activity, kinase activity, phosphatase activity, nucleic acid processing activity, GTPase activity, guanine nucleotide exchange activity, GTPase activating activity, etc.). Preferred panels also include libraries of receptors or ligands (e.g., panels of G-protein coupled receptors, tyrosine kinase receptors, nuclear hormone receptors, cell adhesion molecules (integrins, VCAM, CD4, CD8), major histocompatibility complex proteins, nicotinic receptors, etc.). Preferred panels also include libraries of cells, cell membranes, membrane fragments, reconstituted membranes, organelles, etc. from different sources (e.g., from different cell types, cell lines, tissues, organisms, activation states, etc.).

Applications of panels include the determination of a state of a biological system, the detection or identification of disease state. The determination of analytes associated with a state of a biological system (e.g., by differential measurements of a plurality of analytes in samples derived from normal or diseased biological systems or from normal and activated biological systems, etc.). Panels may also be employed in drug screening. Through the use of panels, the effect of a potential drug on a plurality of biological activities (e.g., binding interactions or enzymatic activities) can be determined in one well of a MDMW Plate. Panels may also be used to speed up the characterization of a protein. For example a protein may be screened against a library of biological materials to identify biological materials that bind the protein, accept the protein as an enzymatic substrate, are modified by an enzymatic activity of the protein, or otherwise interact with the protein. Conversely, a biological material may be screened against a library of proteins to identify the proteins that bind the biological material, accept the biological material as an enzymatic substrate, are modified by an activity of the biological material, or otherwise interact with the biological material.

Figure 2:
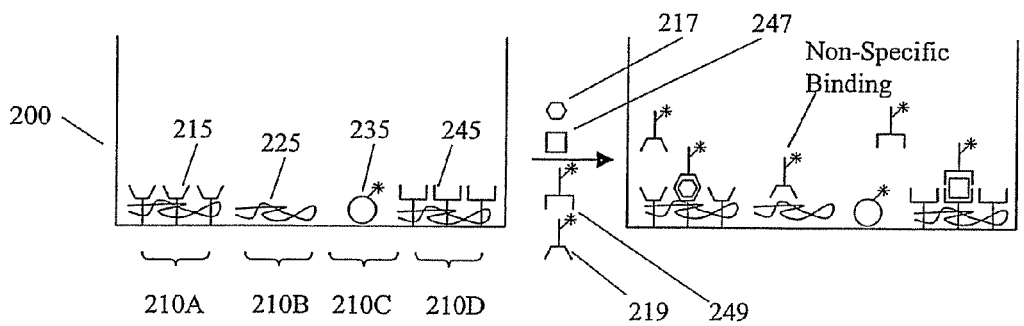
FIG. 2 is a schematic representation, according to one embodiment of the invention, of an assay panel that includes a test binding assay, a control for non-specific binding, a control for the efficiency of signal generation and transmission, and a control binding assay.

Some assay domains in an assay cell or well may be reserved for assay controls or calibrators. FIG. 2 is a schematic representation, according to one embodiment of the invention, of an assay panel that includes a test binding assay for an analyte of interest, a control for non-specific binding, a control for the efficiency of signal generation and transmission, and a control binding assay. FIG. 2 shows a well 200 of a MDMW Plate having assay domains 210A-D. Assay domain 210A comprises a capture binding reagent 215 (e.g., an antibody or a nucleic acid) specific for the analyte of interest 217. Assay domain 210B comprises a blocking agent 225 (e.g., BSA, or bovine IgG) that, preferably, was also used to block open sites in assay domain 210A. Alternatively, blocking agent 225 is a reagent with similar properties to capture binding reagent 215 except that it is not expected to interact with samples introduced into the assay. Assay domain 210C comprises a labeled reagent 235. Assay domain 210D comprises a capture binding reagent 245 specific for control analyte 247. The well also comprises labeled detection antibody 219 that is specific for analyte 215, labeled detection antibody 249 that is specific for control analyte 247, an unknown quantity of analyte 217, and a predetermined amount of control analyte 247. Formation of a sandwich complex in assay domain 210A allows for measurement of the analyte. Assay domain 210B is used to measure the amount of background signal including non-specific binding of the labeled reagents. Assay domain 210C is used to control for factors that influence the efficiency of signal generation by the label and the efficiency of signal detection. Measurement of a sandwich complex in assay domain 210D is used to control for factors that influence the efficiency of binding reactions. In alternate embodiments, assay domains 210A and/or 210D comprise reagents for conducting other types of measurements such as other binding assay formats or enzymatic activity assays.

Figure 3:
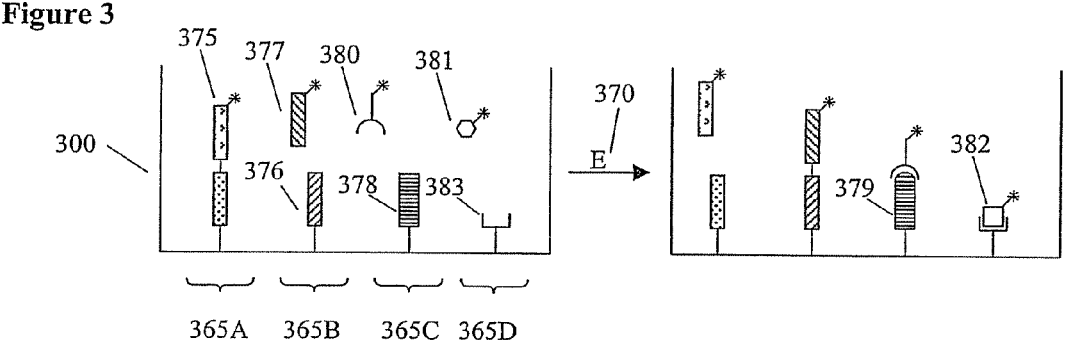
FIG. 3 is a schematic representation, according to one embodiment of the invention, of an assay panel that includes assays for several activities of an enzyme with a plurality of activities.

FIG. 3 illustrates an assay, according to one embodiment of the invention, for the activities of an enzyme with multiple activities. The assay is carried out in well 300 of a MDMW Plate. Enzyme 370 cleaves labeled substrate 375 (immobilized in assay domain 365A) to release a labeled product from the assay domain. Enzyme 370 also joins substrate 376 (immobilized in assay domain 365B) and labeled substrate 377 to link the label to the assay domain. Enzyme 370 also modifies substrate 378 (immobilized in assay domain 365C) to make a product 379 that is recognized by labeled binding reagent 380. Enzyme 370 also catalyzes the conversion of labeled substrate 381 to labeled product 382. Labeled product 382 is then captured by binding reagent 383 (immobilized in assay domain 365D). In an alternate embodiment, the label is omitted from substrate 381 and product 382 is detected by addition of a labeled detection binding reagent to form a sandwich complex.

Figure 4:
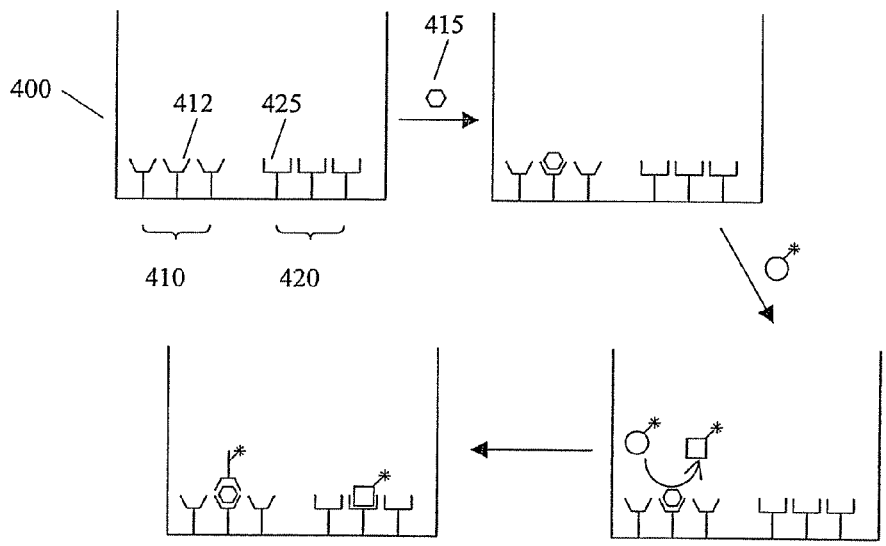
FIG. 4 is a schematic representation, according to one embodiment of the invention, of an assay panel comprising a binding assay for an enzyme and a binding assay for an enzyme product.

FIG. 4 illustrates an assay, according to one embodiment of the invention, of an enzymatic activity. Well 400 of a MDMW Plate comprises assay domain 410 having an immobilized capture binding reagent 412 (e.g., an antibody) capable of binding enzyme 415 and assay domain 420 comprising an immobilized binding reagent 425 (e.g., an antibody) capable of binding a product of enzyme 415. Addition of a sample containing the enzyme leads to the capture of the enzyme in assay domain 420. Optionally, a wash step may be introduced to remove interfering substances in the enzyme sample. Addition of a labeled substrate results in the generation of a labeled product that is captured and measured in assay domain 420. Addition of labeled detection reagent 417 (e.g., an antibody) allows for the measurement of the amount of enzyme 415 in assay domain 410 via sandwich binding assay. This measurement allows the measured enzymatic activity to be referenced to the amount of enzyme. Alternatively, enzyme 410 is labeled and labeled detection reagent 417 may be omitted. In another alternative embodiment, labeled detection reagent 417 is omitted and enzyme 415 is captured and, optionally, purified but not directly measured. In a preferred embodiment of the assay, enzyme 415 is a phosphatase or kinase and binding reagent 425 is an antibody that preferentially binds to one of a phospho-peptide or its nonphosphorylated form.

Figure 5:
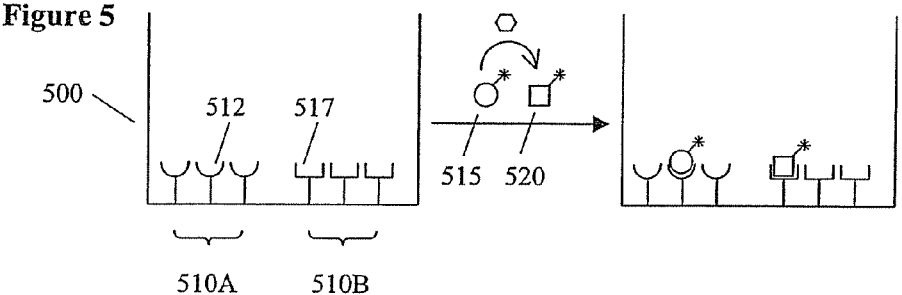
FIG. 5 is a schematic representation, according to one embodiment of the invention, of an assay panel comprising binding assays for the substrate and product of an enzymatic reaction.

FIG. 5 illustrates an assay, according to one embodiment of the invention, where an enzymatic activity is measured by measuring the consumption of substrate and the generation of product. Well 500 in a MDMW Plate comprises an assay domain 510A comprising immobilized capture binding reagent 512 specific for labeled enzyme substrate 515 and an assay domain 510B comprising immobilized capture binding reagent 517 specific for labeled enzyme product 520. A sample comprising a mixture of labeled substrate 515 and labeled product 520 resulting from the action of an enzyme on the enzyme substrate is introduced into well 500. Measurement of substrate and product by binding assay allows the extent of conversion to be calculated even if the initial amount of substrate was unknown. Alternatively, substrate 515 is not labeled and substrate 515 and product 520 are measured via sandwich binding assay or competitive binding assay. In a preferred embodiment of the invention, the enzyme is a kinase or phosphatase and the binding reagents are antibodies specific for the phosphorylated or non-phosphorylated form of a peptide or protein. Alternatively, one capture reagent is specific for either product or substrate and the other capture reagent binds both equally. This panel allows the measurement of product or substrate in one domain and the combined total of product and substrate in the other domain.

Figure 6:
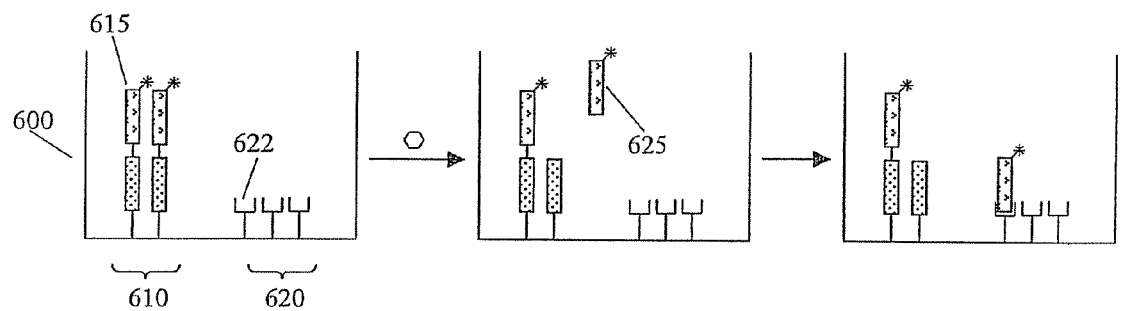
FIG. 6 is a schematic representation, according to one embodiment of the invention, of an assay panel for a cleaving enzyme comprising an assay domain having a labeled substrate for the enzyme and an assay domain comprising a binding reagent capable of capturing a labeled product of the invention.

FIG. 6 illustrates an assay, according to one embodiment of the invention, for an enzyme with a cleaving activity. Well 600 of a MDMW Plate comprises assay domain 610 comprising an immobilized labeled substrate 615 and assay domain 620 comprising an immobilized binding reagent 622 that is specific for labeled enzyme product 625. Enzyme 630 cleaves substrate 615 forming product 625 which is captured in assay domain 620. The assay format allows the measurement of both the consumption of substrate and the production of product. Optionally, substrate 615 is not labeled and product 625 is measured via a sandwich or competitive binding assay. In a preferred embodiment, enzyme 630 is a protease, substrate 615 is a labeled peptide, and binding reagent 622 is an antibody specific for the peptide. Alternatively, substrate 615 also comprises a capture moiety and binding reagent 622 is specific for the capture moiety.

Figure 7:
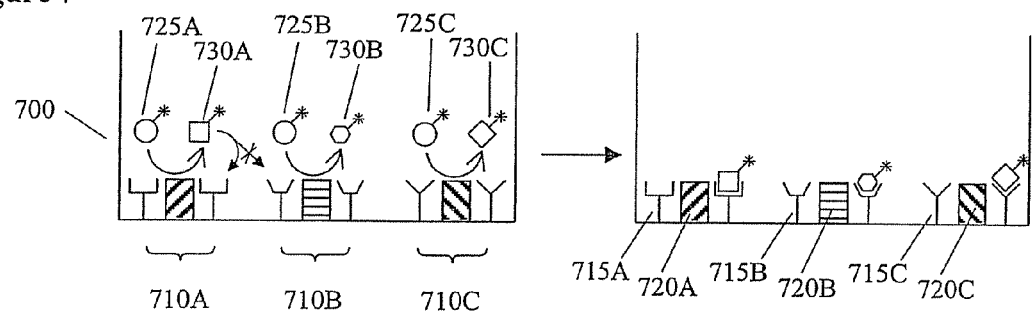
FIG. 7 is a schematic representation, according to one embodiment of the invention, of an assay panel comprising an array of assay domains comprising different enzymes, the enzymes being co-immobilized for binding reagents capable of binding enzymatic products.

FIG. 7 illustrates an assay format, according to one embodiment of the invention, for measuring the activity of an immobilized array of enzymes. Well 700 of a MDMW Plate comprises assay domains 710A-C which comprise immobilized enzymes 715A-C and immobilized binding reagents 720A-C, the binding reagents being specific for a product of the enzyme co-immobilized in the same assay domain. Introduction of labeled substrates 725A-C (which may the same or different) leads to the generation of labeled products 730A-C (which may be the same or different). The close proximity of the enzymes to binding reagents leads to preferential capture of products in the assay domain in which they were produced (as opposed to the diffusion and capture of products in adjacent domains). Preferably, the assay domains are in slight depressions in the bottom of the well so as to inhibit convection near the surface of the domains and to inhibit horizontal diffusion away from the surface of the domains. In an alternate embodiment, the substrates are not labeled and the product is measured via a sandwich or competitive binding assay. In one preferred embodiment, the enzymes are kinases, the substrates have consensus sequences for specific members of the kinase library, and the binding reagents are antibodies specific for the product of the enzymes with which they are co-immobilized. Alternatively, the binding reagents are broadly specific for phosphopeptides (e.g., an anti-phosphotyrosine or an anti-phosphoserine antibody). In another preferred embodiment, the enzymes are kinases, the substrates are the same and are a generic kinase substrate, and the binding reagents are the same and are binding reagents broadly specific for phosphopeptides (e.g., an anti-phosphotyrosine or an anti-phosphoserine antibody).

FIGS. 8A-8C illustrate expanded dynamic range binding assays, according to preferred embodiments of the invention, comprising three assay domains of varying affinity for the analyte of interest. This assay format is particularly advantageous when the dynamic range must extend to analyte concentrations that are greater than the binding capacity of assay domains in a well. Well 800 in a MDMW Plate comprises assay domains 810A-C for measuring analyte 820, the well comprising i) assay domain 810A comprising immobilized binding reagent 815A, binding reagent 815A having a dissociation constant for analyte=$K_d^a$, ii) assay domain 810B comprising immobilized binding reagent 815B, binding reagent 815B having a dissociation constant for analyte=$K_d^b$ and iii) assay domain 810C comprising immobilized binding reagent 815C, binding reagent 815C having a dissociation constant for analyte=$K_d^c$, wherein $K_d^a < K_d^b < K_d^c$ and wherein $K_d^b$ and $K_d^c$ are, preferably, greater than the concentration of analyte needed to saturate assay domain 810A. A labeled analyte 820 is introduced into the well. Preferably, the dissociation constants differ by a factor of 10 or more so that: i) when the concentration of analyte is $\ll K_d^b$, only assay domain 810A will be significantly populated (FIG. 8A); ii) when the concentration of analyte is $\sim K_d^b$, assay domain 810A will be saturated, assay domain 810B will be partially populated, and assay domain 810C will be negligibly populated (FIG. 8B); and iii) when the concentration of analyte is $\sim K_d^c$, assay domains 810A and 810B will be saturated and assay domain 810C will be partially populated (FIG. 8C). In each concentration range, the signal from the partially populated assay domain is used to quantitate analyte. Optionally, assay domain 810C is omitted or additional assay domains are included for extending the dynamic range into additional concentration ranges.

FIGS. 9A-9B illustrate expanded dynamic range binding assays, according to preferred embodiment of the inventions, comprising a sandwich binding assay and a competitive binding assay for the same analyte. This assay format is particularly advantageous when the dynamic range must extend to analyte concentrations that are greater than the binding capacity of assay domains in a well. Well 900 in a MDMW Plate comprises i) assay domain 910 comprising an immobilized capture binding reagent 912 that is specific for analyte 915 and ii) assay domain 920 comprising an immobilized competitor 925 that competes with analyte 915 for binding to labeled binding reagent 917. Introduction of analyte 915 and labeled binding reagent 917 leads to the binding of labeled binding reagent 917 to assay domain 910 via a sandwich complex and to assay domain 920 via direct binding. Preferably, the amount of capture binding reagent 912 is roughly the same as the amount of competitor 925 and is roughly half of the amount of labeled binding reagent 917. For amounts of analyte less than the amount of capture binding reagent (i.e., the binding capacity of assay domain 910), the amount of label bound to assay domain 910 is roughly proportional to the amount of analyte and the amount of label bound to assay domain 920 is roughly constant and saturated (FIG. 9A). For amounts of analyte greater than the amount of capture binding reagent, the amount of label bound to assay domain 910 decrease with increasing analyte due to the "hook effect" and the amount of label bound to assay domain 920 also decreases due to competitive binding (FIG. 9B). The competitive assay can therefore be used to quantitate analyte at high concentrations of analyte or simply to provide warning that the sandwich assay has exceeded its dynamic range. In a preferred embodiment, analyte 915 is a protein and binding reagents 912 and 917 are antibodies specific for different epitopes on analyte 915. Competitor 925 may be a labeled version of analyte 915 or, more preferably, is a peptide that binds to binding reagent 917 but not binding reagent 912 (thereby, reducing the possibility of binding reagent 912 or competitor 925 leaching from the surface and binding).

According to preferred embodiments of the invention, the assay domains of the invention are incorporated in assay modules or plates adapted for electrode induced luminescence (preferably, electrochemiluminescence) assays, e.g., assay domains are supported on one or more integrated electrodes within an assay cell (e.g., the well of a MDMW plate). Suitable assay modules and well plates, and methods of using such assay modules and plates and systems incorporating the same are set forth in U.S. application Ser. Nos. 10/185,274 and 10/185,363, entitled "Assay Plates, Reader Systems and Methods for Luminescence Test Measurements", filed Jun. 28, 2002 (see Sections 3, 4 and 5.1-5.6), hereby incorporated by reference. According to one preferred embodiment of the invention, an assay module or plate comprises one or more (preferably two or more, 6 or more, 24 or more, 96 or more, 384 or more, 1536 or more or 9600 or more) assay wells, assay chambers and/or assay domains (e.g., discrete locations on a module surface where an assay reaction occurs and/or where an assay signal is emitted; typically an electrode surface, preferably a working electrode surface). According to an even more preferred embodiment, the assay module is a multi-well assay plate having a standard well configuration (e.g., 6 well, 24 well, 96 well, 384 well, 1536 well, 6144 well or 9600 well). The wells of such plates can further comprise a plurality (e.g., 2 or more, 4 or more, 7 or more, 25 or more, 64 or more, 100 or more, etc.) of discrete assay domains.

One aspect of the invention relates to improved assay modules (e.g., plates) adapted for use in assays, preferably luminescence assays, more preferably electrode induced luminescence assays, even more preferably electrochemiluminescence assays. The assay modules of the invention are preferably suitable not only for ECL assays, but also suitable for fluorescence assays, chemiluminescence assays, bioluminescence assays, phosphorescence assays, optical transmittance assays (e.g., measurements of optical density or light scattering) and electrochemical assays (e.g., wherein the measurement involves measuring current or voltage).

According to one preferred embodiment of the invention, an assay module or plate comprises one or more (preferably two or more, 6 or more, 24 or more, 96 or more, 384 or more, 1536 or more or 9600 or more) assay wells, assay chambers and/or assay domains (e.g., discrete locations on a module surface where an assay reaction occurs and/or where an assay signal is emitted; typically an electrode surface, preferably a working electrode surface). According to a particularly preferred embodiment, the assay plate is a multi-well assay plate having a standard well configuration (e.g., 6 well, 24 well, 96 well, 384 well, 1536 well, 6144 well or 9600 well).

An electrode induced luminescence well (preferably electrochemiluminescence well (i.e., a well adapted for electrochemiluminescence)) or electrode induced luminescence domain (preferably electrochemiluminescence assay domain (i.e., an assay domain adapted for electrochemiluminescence assays)) may include a first electrode surface (such as a working electrode surface) and, preferably also includes a second electrode surface (such as a counter electrode surface).

The invention also relates to a multi-well module, preferably an assay plate, for conducting one or more assays, the module having a plurality of wells (and/or chambers), wherein two or more of the plurality of wells (and/or chambers) comprise at least one first electrode surface and, preferably at least one counter electrode surface. According to a preferred embodiment, two or more of the plurality of wells (and/or chambers) comprise a working electrode surface and, preferably a counter electrode surface, adapted to induce luminescence in the wells. The invention also relates to a multi-well module, preferably a plate, for conducting one or more assays, the module having a plurality of wells, wherein one or more of the plurality of wells comprise a working electrode surface and a counter electrode surface adapted to induce luminescence in the wells. Preferably, all or substantially all of the wells comprise an electrode surface.

Another embodiment relates to a multi-well assay module, preferably an assay plate, for conducting electrode induced luminescence (preferably electrochemiluminescence) assays, the module, preferably a plate, having a plurality of wells, wherein each of the plurality of wells comprises at least one first electrode surface (e.g., a working electrode) and, preferably, at least one second electrode surface (e.g., a counter electrode).

Another embodiment relates to an assay plate for conducting one or more electrode induced luminescence (preferably electrochemiluminescence) assays, the plate having a plurality of wells or assay regions comprising electrode surfaces, wherein the electrode surfaces consist essentially of at least one working electrode surface and at least one counter electrode surface.

Preferably, the assay regions or assay wells are free of reference electrodes allowing for a greater density of assay domains and simplified instrumentation for inducing and measuring luminescence.

One aspect of the invention relates to improved assay modules (e.g., plates) adapted for use in assays, preferably luminescence assays, more preferably electrode induced luminescence assays, even more preferably electrochemiluminescence assays. The assay modules of the invention are preferably suitable not only for ECL assays, but also suitable for fluorescence assays, chemiluminescence assays, bioluminescence assays, phosphorescence assays, optical transmittance assays (e.g., measurements of optical density or light scattering) and electrochemical assays (e.g., wherein the measurement involves measuring current or voltage).

According to one preferred embodiment of the invention, an assay module or plate comprises one or more (preferably two or more, 6 or more, 24 or more, 96 or more, 384 or more, 1536 or more or 9600 or more) assay wells, assay chambers and/or assay domains (e.g., discrete locations on a module surface where an assay reaction occurs and/or where an assay signal is emitted; typically an electrode surface, preferably a working electrode surface). According to a particularly preferred embodiment, the assay plate is a multi-well assay plate having a standard well configuration (e.g., 6 well, 24 well, 96 well, 384 well, 1536 well, 6144 well or 9600 well).

An electrode induced luminescence well (preferably electrochemiluminescence well (i.e., a well adapted for electrochemiluminescence)) or electrode induced luminescence domain (preferably electrochemiluminescence assay domain (i.e., an assay domain adapted for electrochemiluminescence assays)) may include a first electrode surface (such as a working electrode surface) and, preferably also includes a second electrode surface (such as a counter electrode surface).

The invention also relates to a multi-well module, preferably an assay plate, for conducting one or more assays, the module having a plurality of wells (and/or chambers), wherein two or more of the plurality of wells (and/or chambers) comprise at least one first electrode surface and, preferably at least one counter electrode surface. According to a preferred embodiment, two or more of the plurality of wells (and/or chambers) comprise a working electrode surface and, preferably a counter electrode surface, adapted to induce luminescence in the wells. The invention also relates to a multi-well module, preferably a plate, for conducting one or more assays, the module having a plurality of wells, wherein one or more of the plurality of wells comprise a working electrode surface and a counter electrode surface adapted to induce luminescence in the wells. Preferably, all or substantially all of the wells comprise an electrode surface.

Another embodiment relates to a multi-well assay module, preferably an assay plate, for conducting electrode induced luminescence (preferably electrochemiluminescence) assays, the module, preferably a plate, having a plurality of wells, wherein each of the plurality of wells comprises at least one first electrode surface (e.g., a working electrode) and, preferably, at least one second electrode surface (e.g., a counter electrode).

Another embodiment relates to an assay plate for conducting one or more electrode induced luminescence (preferably electrochemiluminescence) assays, the plate having a plurality of wells or assay regions comprising electrode surfaces, wherein the electrode surfaces consist essentially of at least one working electrode surface and at least one counter electrode surface.

Preferably, the assay regions or assay wells are free of reference electrodes allowing for a greater density of assay domains and simplified instrumentation for inducing and measuring luminescence.

The working electrode surface area may be smaller, the same or larger than the counter electrode surface area. In some embodiments, the working electrode surface is preferably much larger than the counter electrode surface. This configuration allows for a greater working electrode surface on which to immobilize assay reagents. Preferably, the surface ratio of the working electrode surface to the counter electrode surface is at least 2 to 1, more preferably at least 5 to 1, even more preferably at least 10 to 1, still more preferred at least 50 to 1, even more preferably at least 100 to 1 and most preferred at least 500 to 1. Surprisingly, the assay modules of the invention provide for the performance of electrochemiluminescence assays with very little counter electrode surface. Preferably, the working electrode is substantially centered within the well so as to maximize the percentage of ECL emitted from the electrode that can be captured by a light detector placed above the well.

According to another embodiment, the first electrode surface (e.g., working electrode surface) is centered at the bottom of each well and the second electrode surface (e.g., counter electrode surface) is adjacent the periphery of the bottom of each well. In some embodiments, the working electrode surface is centered at the bottom of each well and is completely surrounded by the counter electrode surface.

Alternatively, for some applications it is desirable that working electrode surfaces be small, e.g., relative to the surface area of a well or well bottom. In some applications, this configuration may reduce non-specific signals. According to one embodiment of the invention, the multi-well assay module has a plurality of wells, each well having a well bottom comprising a first electrode surface, a second electrode surface and a dielectric surface (preferably the dielectric surface is the surface of the bottom of the well between the first electrode surface and the second electrode surface), wherein the ratio of the first electrode surface and the dielectric surface (or alternatively the surface of the well bottom) is less than 1 to 5, preferably 1 to 10, more preferably 1 to 30.

According to one preferred embodiment of the invention, the assay module comprises a first electrode surface (preferably a working electrode surface) that is bounded by a dielectric surface, the dielectric surface being raised or lowered (preferably, raised) and/or of different hydrophobicity (preferably, more hydrophobic) than the electrode surface. Preferably, the dielectric boundary is higher, relative to the electrode surface, by 0.5-100 micrometers, or more preferably by 2-30 micrometers, or most preferably by 8-12 micrometers. Even more preferably, the dielectric boundary has a sharply defined edge (i.e., providing a steep boundary wall and/or a sharp angle at the interface between the electrode and the dielectric boundary). Preferably, the first electrode surface has a contact angle for water 10 degrees less than the dielectric surface, preferably 15 degrees less, more preferably 20 degrees less, more preferably 30 degrees less, even more preferably 40 degrees less, and most preferred 50 degrees less. One advantage of having a dielectric surface that is raised and/or more hydrophobic than the electrode surface is in the reagent deposition process where the dielectric boundary may be used to confine a reagent within the boundary of the electrode surface. In particular, having a sharply defined edge with a steep boundary wall and/or a sharp angle at the interface between the electrode and dielectric boundary is especially useful for "pinning" drops of solution and confining them to the electrode surface.

According to another embodiment, an assay module comprises one or more (preferably two or more) wells, the wells having one or more first electrode surfaces (preferably one or more working electrode surfaces) and a plurality of assay domains immobilized therein. Preferably, at least two of the plurality of the assay domains comprises different binding reagents. Preferably, each well comprises at least four, more preferably at least seven, even more preferably at least ten assay domains and most preferred at least 15 assay domains. One preferred embodiment is a 24 well plate wherein each well comprises at least 16, preferably at least 25, more preferably at least 64, even more preferably at least 100 assay domains per well and most preferably at least 250 assay domains per well.

Another embodiment of the invention relates to a multi-well module (preferably a multi-well plate) having a plurality of wells, wherein the wells comprise a plurality of working electrode surfaces having assay domains immobilized thereon. Preferably, the assay domains are independently addressable. For example, a well may comprise a plurality of assay domains, wherein each assay domain comprises an electrode which is independently addressable from the other assay domains within the well. In another example, a group of wells may each comprise a plurality of assay domains, wherein each assay domain comprises an electrode which is independently addressable from the other assay domains within the well, but which is jointly addressable with an assay domain in each of the other wells.

Alternatively, for some applications it is desirable that working electrode surfaces be small, e.g., relative to the surface area of a well or well bottom. In some applications, this configuration may reduce non-specific signals. According to one embodiment of the invention, the multi-well assay module has a plurality of wells, each well having a well bottom comprising a first electrode surface, a second electrode surface and a dielectric surface (preferably the dielectric surface is the surface of the bottom of the well between the first electrode surface and the second electrode surface), wherein the ratio of the first electrode surface and the dielectric surface (or alternatively the surface of the well bottom) is less than 1 to 5, preferably 1 to 10, more preferably 1 to 30.

According to one preferred embodiment of the invention, the assay module comprises a first electrode surface (preferably a working electrode surface) that is bounded by a dielectric surface, the dielectric surface being raised or lowered (preferably, raised) and/or of different hydrophobicity (preferably, more hydrophobic) than the electrode surface. Preferably, the dielectric boundary is higher, relative to the electrode surface, by 0.5-100 micrometers, or more preferably by 2-30 micrometers, or most preferably by 8-12 micrometers. Even more preferably, the dielectric boundary has a sharply defined edge (i.e., providing a steep boundary wall and/or a sharp angle at the interface between the electrode and the dielectric boundary). Preferably, the first electrode surface has a contact angle for water 10 degrees less than the dielectric surface, preferably 15 degrees less, more preferably 20 degrees less, more preferably 30 degrees less, even more preferably 40 degrees less, and most preferred 50 degrees less. One advantage of having a dielectric surface that is raised and/or more hydrophobic than the electrode surface is in the reagent deposition process where the dielectric boundary may be used to confine a reagent within the boundary of the electrode surface. In particular, having a sharply defined edge with a steep boundary wall and/or a sharp angle at the interface between the electrode and dielectric boundary is especially useful for "pinning" drops of solution and confining them to the electrode surface.

According to another embodiment, an assay module comprises one or more (preferably two or more) wells, the wells having one or more first electrode surfaces (preferably one or more working electrode surfaces) and a plurality of assay domains immobilized therein. Preferably, at least two of the plurality of the assay domains comprises different binding reagents. Preferably, each well comprises at least four, more preferably at least seven, even more preferably at least ten assay domains and most preferred at least 15 assay domains. One preferred embodiment is a 24 well plate wherein each well comprises at least 16, preferably at least 25, more preferably at least 64, even more preferably at least 100 assay domains per well and most preferably at least 250 assay domains per well.

Another embodiment of the invention relates to a multi-well module (preferably a multi-well plate) having a plurality of wells, wherein the wells comprise a plurality of working electrode surfaces having assay domains immobilized thereon. Preferably, the assay domains are independently addressable. For example, a well may comprise a plurality of assay domains, wherein each assay domain comprises an electrode which is independently addressable from the other assay domains within the well. In another example, a group of wells may each comprise a plurality of assay domains, wherein each assay domain comprises an electrode which is independently addressable from the other assay domains within the well, but which is jointly addressable with an assay domain in each of the other wells.

The invention also relates to methods and apparatus for the measurement of signals from assay modules and MDMW plates of the invention. The preferred apparatus of the invention can be used to induce and measure luminescence in assays conducted in assay modules, preferably in multi-well assay plates. It may incorporate, for example, one or more photodetectors; a light tight enclosure; electrical connectors for contacting the assay modules; mechanisms to transport multi-well assay modules into and out of the apparatus (and in particular, into and out of light tight enclosures); mechanisms to align and orient multi-well assay modules with the photodetector(s) and with electrical contacts; mechanisms to track and identify modules (e.g. bar code readers); mechanisms to make electrical connections to modules, one or more sources of electrical energy for inducing luminescence in the modules; and appropriate electronics and software.

The apparatus may also include mechanisms to store, stack, move and/or distribute one or more assay modules (e.g. multi-well plate stackers). The apparatus may advantageously use arrays of photodetectors (e.g. arrays of photodiodes) or imaging photodetectors (e.g. CCD cameras) to measure light. These detectors allow the apparatus to measure the light from multiple wells, assay domains, and/or assay cells simultaneously and/or to image the intensity and spatial distribution of light emitted from an individual well, assay cell and/or assay domain.

The apparatus can preferably measure light from one or more sectors of an assay module, preferably a multi-well assay plate. In some embodiments, a sector comprises a group of wells, assay domains and/or assay cells numbering between one and a number fewer than the total number of wells (and/or chambers) in the assay module (e.g. a row, column, or two-dimensional sub-array of wells in a multi-well plate). In preferred embodiments, a sector comprises between 4 percent and 50 percent of the wells of a multi-well plate. In especially preferred embodiments, multi-well assay plates are divided into columnar sectors (each sector having one row or column of wells) or square sectors (e.g., a standard sized multi-well plate can be divided into six square sectors of equal size). In some embodiments, a sector may comprise one or more wells with more than one fluid containment region within the wells. The apparatus, preferably, is adapted to sequentially induce ECL in and/or sequentially measure ECL from the sectors in a given module, preferably plate.

One aspect of the invention relates to the immobilization of materials in assay domains on electrodes having improved electrode compositions and surfaces and assay modules comprising these electrode compositions and surfaces. Electrodes in the present invention are preferably comprised of a conductive material. The electrode may comprise a metal such as gold, silver, platinum, nickel, steel, iridium, copper, aluminum, a conductive alloy, or the like. They may also comprise oxide coated metals (e.g. aluminum oxide coated aluminum). Electrodes may comprise non-metallic conductors such as conductive forms of molecular carbon. Electrodes may also be comprised of semiconducting materials (e.g. silicon, germanium) or semi-conducting films such as indium tin oxide (ITO), antimony tin oxide (ATO) and the like. Electrodes may also be comprised of mixtures of materials containing conducting composites, inks, pastes, polymer blends, metal/non-metal composites and the like. Such mixtures may include conductive or semi-conductive materials mixed with non-conductive materials. Preferably, electrode materials are substantially free of silicone-based materials.

Electrodes (in particular working electrodes) used in assay modules of the invention are advantageously able to induce luminescence from luminescent species. Preferable materials for working electrodes are materials able to induce electrochemiluminescence from Ruthenium-tris-bipyridine in the presence of tertiary alkyl amines (such as tripropyl amine). Examples of such preferred materials include platinum, gold, ITO, carbon, carbon-polymer composites, and conductive polymers.

Preferably, electrodes are comprised of carbon-based materials such as carbon, carbon black, graphitic carbon, carbon nanotubes, carbon fibrils, graphite, carbon fibers and mixtures thereof. Advantageously, they may be comprised of conducting carbon-polymer composites, conducting particles dispersed in a matrix (e.g. carbon inks, carbon pastes, metal inks), and/or conducting polymers. One preferred embodiment of the invention is an assay module, preferably a multi-well plate, having electrodes (e.g., working and/or counter electrodes) that comprise carbon, preferably carbon layers, more preferably screen-printed layers of carbon inks. Some useful carbon inks include materials produced by Acheson Colloids Co. (e.g., Acheson 440B, 423ss, PF407A, PF407C, PM-003A, 30D071, 435A, Electrodag 505SS, and Aquadag™), E. I. Du Pont de Nemours and Co. (e.g., Dupont 7105, 7101, 7102, 7103, 7144, 7082, 7861D, and CB050), Conductive Compounds Inc (e.g., C-100), and Ercon Inc. (e.g., G-451).

In another preferred embodiment, the electrodes of the invention comprise carbon fibrils. The terms "carbon fibrils", "carbon nanotubes", single wall nanotubes (SWNT), multi-wall nanotubes (MWNT), "graphitic nanotubes", "graphitic fibrils", "carbon tubules", "fibrils" and "buckeytubes", all of which terms may be used to describe a broad class of carbon materials (see Dresselhaus, M. S.; Dresselhaus, G.; Eklund, P. C.; "Science of Fullerenes and Carbon Nanotubes", Academic Press, San Diego, Calif., 1996, and references cited therein). The terms "fibrils" and "carbon fibrils" are used throughout this application to include this broad class of carbon-based materials. Individual carbon fibrils as disclosed in U.S. Pat. Nos. 4,663,230; 5,165,909; and 5,171,560 are particularly advantageous. They may have diameters that range from about 3.5 nm to 70 nm, and length greater than $10^2$ times the diameter, an outer region of multiple, essentially continuous, layers of ordered carbon atoms and a distinct inner core region. Simply for illustrative purposes, a typical diameter for a carbon fibril may be approximately between about 7 and 25 nm, and a typical range of lengths may be 1000 nm to 10,000 nm. Carbon fibrils may also have a single layer of carbon atoms and diameters in the range of 1 nm-2 nm. Electrodes of the invention may comprise one or more carbon fibrils, e.g., in the form of a fibril mat, a fibril aggregate, a fibril ink, a fibril composite (e.g., a conductive composite comprising fibrils dispersed in an oil, paste, ceramic, polymer, etc.). One preferred embodiment of the invention relates to a multi-well plate comprising a substrate comprising a carbon nanotube-containing composite (preferably, carbon nanotubes dispersed in a polymeric matrix), wherein the surface of the substrate is etched to expose the carbon nanotubes, thereby forming one or more working electrodes.

Electrodes may be formed into patterns by a molding process (i.e., during fabrication of the electrodes), by patterned deposition, by patterned printing, by selective etching, through a cutting process such as die cutting or laser drilling, and/or by techniques known in the art of electronics microfabrication. Electrodes may be self supporting or may be supported on another material, e.g. on films, plastic sheets, adhesive films, paper, backings, meshes, felts, fibrous materials, gels, solids (e.g. metals, ceramics, glasses), elastomers, liquids, tapes, adhesives, other electrodes, dielectric materials and the like. The support may be rigid or flexible, flat or deformed, transparent, translucent, opaque or reflective. Preferably, the support comprises a flat sheet of plastic such as acetate or polystyrene. Electrode materials may be applied to a support by a variety of coating and deposition processes known in the art such as painting, spray-coating, screen-printing, ink jet printing, laser printing, spin-coating, evaporative coating, chemical vapor deposition, etc. Supported electrodes may be patterned using photolithographic techniques (e.g., established techniques in the microfabrication of electronics), by selective etching, and/or by selective deposition (e.g., by evaporative or CVD processes carried out through a mask). In a preferred embodiment, electrodes are comprised of extruded films of conducting carbon/polymer composites. In another preferred embodiment, electrodes are comprised of a screen printed conducting ink deposited on a substrate. Electrodes may be supported by another conducting material. Advantageously, screen printed carbon ink electrodes are printed over a conducting metal ink (e.g., silver ink) layer so as to improve the conductivity of the electrodes.

According to one preferred embodiment of the invention, the electrode surface (preferably a working electrode surface of an assay module or assay plate) is bounded by a dielectric surface, the dielectric surface being raised or lowered (preferably, raised) and/or of different hydrophobicity (preferably, more hydrophobic) than the electrode surface. Preferably, the dielectric boundary is higher, relative to the electrode surface, by 0.5-100 micrometers, or more preferably by 2-30 micrometers, or most preferably by 8-12 micrometers. Even more preferably, the dielectric boundary has a sharply defined edge (i.e., providing a steep boundary wall and/or a sharp angle at the interface between the electrode and the dielectric boundary).

Preferably, the first electrode surface has a contact angle for water 10 degrees less than the dielectric surface, preferably 15 degrees less, more preferably 20 degrees less, more preferably 30 degrees less, even more preferably 40 degrees less, and most preferred 50 degrees less. One advantage of having a dielectric surface that is raised and/or more hydrophobic than the electrode surface is in the reagent deposition process where the dielectric boundary may be used to confine a reagent within the boundary of the electrode surface. In particular, having a sharply defined edge with a steep boundary wall and/or a sharp angle at the interface between the electrode and dielectric boundary is especially useful for "pinning" drops of solution and confining them to the electrode surface. In an especially preferred embodiment of the invention, the dielectric boundary is formed by printing a patterned dielectric ink on and/or around the electrode, the pattern designed so as to expose one or more assay domains on the electrode.

Electrodes may be modified by chemical or mechanical treatment to improve the immobilization of reagents. The surface may be treated to introduce functional groups for immobilization of reagents or to enhance its adsorptive properties. Surface treatment may also be used to influence properties of the electrode surface, e.g., the spreading of water on the surface or the kinetics of electrochemical processes at the surface of the electrode. Techniques that may be used include exposure to electromagnetic radiation, ionizing radiation, plasmas or chemical reagents such as oxidizing agents, electrophiles, nucleophiles, reducing agents, strong acids, strong bases and/or combinations thereof. Treatments that etch one or more components of the electrodes may be particularly beneficial by increasing the roughness and therefore the surface area of the electrodes. In the case of composite electrodes having conductive particles or fibers (e.g., carbon particles or fibrils) in a polymeric matrix or binder, selective etching of the polymer may be used to expose the conductive particles or fibers.

One particularly useful embodiment is the modification of the electrode, and more broadly a material incorporated into the present invention by treatment with a plasma, specifically a low temperature plasma, also termed glow-discharge. The treatment is carried out in order to alter the surface characteristics of the electrode, which come in contact with the plasma during treatment. Plasma treatment may change, for example, the physical properties, chemical composition, or surface-chemical properties of the electrode. These changes may, for example, aid in the immobilization of reagents, reduce contaminants, improve adhesion to other materials, alter the wettability of the surface, facilitate deposition of materials, create patterns, and/or improve uniformity. Examples of useful plasmas include oxygen, nitrogen, argon, ammonia, hydrogen, fluorocarbons, water and combinations thereof. Oxygen plasmas are especially preferred for exposing carbon particles in carbon-polymer composite materials. Oxygen plasmas may also be used to introduce carboxylic acids or other oxidized carbon functionality into carbon or organic materials (these may be activated, e.g., as active esters or acyl chlorides) so as to allow for the coupling of reagents. Similarly, ammonia-containing plasmas may be used to introduce amino groups for use in coupling to assay reagents.

Treatment of electrode surfaces may be advantageous so as to improve or facilitate immobilization, change the wetting properties of the electrode, increase surface area, increase the binding capacity for the immobilization of reagents (e.g., lipid, protein or lipid/protein layers) or the binding of analytes, and/or alter the kinetics of electrochemical reactions at the electrode. In some applications, however, it may be preferable to use untreated electrodes. For example, we have found that it is advantageous to etch carbon ink electrodes prior to immobilization when the application calls for a large dynamic range and therefore a high binding capacity per area of electrode. We have discovered that oxidative etching (e.g., by oxygen plasma) has additional advantages in that the potential for oxidation of tripropyl amine (TPA) and the contact angle for water are both reduced relative to the unetched ink. The low contact angle for water allows reagents to be adsorbed on the electrode by application of the reagents in a small volume of aqueous buffer and allowing the small volume to spread evenly over the electrode surface. Surprisingly, we have found that excellent assays may also be carried out on unetched carbon ink electrodes despite the presence of polymeric binders in the ink. In fact, in some applications requiring high sensitivity or low-non specific binding it is preferred to use unetched carbon ink electrodes so as to minimize the surface area of exposed carbon and therefore minimize background signals and loss of reagents from non-specific binding of reagents to the exposed carbon. Depending on the ink used and the process used to apply the ink, the electrode surface may not be easily wettable by aqueous solutions. We have found that we can compensate for the low wettability of the electrodes during the adsorption of reagents by adding low concentrations of non-ionic detergents to the reagent solutions so as to facilitate the spreading of the solutions over the electrode surface. Even spreading is especially important during the localized immobilization of a reagent from a small volume of solution. For example, we have found that the addition of 0.005-0.04% Triton® X-100 allows for the spreading of protein solutions over unetched carbon ink surfaces without affecting the adsorption of the protein to the electrode and without disrupting the ability of a dielectric film applied on or adjacent to the electrode (preferably, a printed dielectric film with a thickness of 0.5-100 micrometers, or more preferably 2-30 micrometers, or most preferably 8-12 micrometers and having a sharply defined edge) to confine fluids to the electrode surface. Preferably, when non-ionic detergents such as Triton® X-100 are used to facilitate spreading of reagents (e.g., capture reagents) onto unetched screen-printed electrodes (i.e., so as to allow the immobilization of the reagents), the solutions containing the reagents are allowed to dry onto the electrode surface. It has been found that this drying step greatly improves the efficiency and reproducibility of the immobilization process.

Electrodes can be derivatized with chemical functional groups that can be used to attach other materials to them. Materials may be attached covalently to these functional groups, or they may be adsorbed non-covalently to derivatized or underivatized electrodes. Electrodes may be prepared with chemical functional groups attached covalently to their surface. These chemical functional groups include but are not limited to COOH, OH, $NH_2$, activated carboxyls (e.g., N-hydroxy succinimide (NHS)-esters), poly-(ethylene glycols), thiols, alkyl $((CH_2)_n)$ groups, and/or combinations thereof). Certain chemical functional groups (e.g., COOH, OH, $NH_2$, SH, activated carboxyls) may be used to couple reagents to electrodes. For further reference to useful immobilization and bioconjugation techniques see G. Hermanson, A. Mallia and P. Smith, *Immobilized Affinity Ligand Techniques* (Academic Press, San Diego, 1992) and G. Hermanson, *Bioconjugate Techniques* (Academic Press, San Diego, 1996).

In preferred embodiments, NHS-ester groups are used to attach other molecules or materials bearing a nucleophilic chemical functional group (e.g., an amine). In a preferred embodiment, the nucleophilic chemical functional group is present on and/or in a biomolecule, either naturally and/or by chemical derivatization. Examples of suitable biomolecules include, but are not limited to, amino acids, proteins and functional fragments thereof, antibodies, binding fragments of antibodies, enzymes, nucleic acids, and combinations thereof. This is one of many such possible techniques and is generally applicable to the examples given here and many other analogous materials and/or biomolecules. In a preferred embodiment, reagents that may be used for ECL may be attached to the electrode via NHS-ester groups.

It may be desirable to control the extent of non-specific binding of materials to electrodes. Simply by way of non-limiting examples, it may be desirable to reduce or prevent the non-specific adsorption of proteins, antibodies, fragments of antibodies, cells, subcellular particles, viruses, serum and/or one or more of its components, ECL labels (e.g., $Ru^{II}(bpy)_3$ and $Ru^{III}(bpy)_3$ derivatives), oxalates, trialkylamines, antigens, analytes, and/or combinations thereof). In another example, it may be desirable to enhance the binding of biomolecules.

One or more chemical moieties that reduce or prevent non-specific binding (also known as blocking groups) may be present in, on, or in proximity to an electrode. Such moieties, e.g., PEG moieties and/or charged residues (e.g., phosphates, ammonium ions), may be attached to or coated on the electrode. Examples of useful blocking reagents include proteins (e.g., serum albumins and immunoglobins), nucleic acids, polyethylene oxides, polypropylene oxides, block copolymers of polyethylene oxide and polypropylene oxide, polyethylene imines and detergents or surfactants (e.g., classes of non-ionic detergents/surfactants known by the trade names of Brij, Triton, Tween, Thesit, Lubrol, Genapol, Pluronic (e.g., F108), Tetronic, Tergitol, and Span).

Materials used in electrodes may be treated with surfactants to reduce non-specific binding. For example, electrodes may be treated with surfactants and/or detergents that are well known to one of ordinary skill in the art (for example, the Tween, Triton, Pluronics (e.g., F108), Span, and Brij series of detergents). Solutions of PEGs and/or molecules which behave in similar fashion to PEG (e.g., oligo- or polysaccharides, other hydrophilic oligomers or polymers) ("Polyethylene glycol chemistry: Biotechnical and Biomedical Applications", Harris, J. M. Editor, 1992, Plenum Press) may be used instead of and/or in conjunction with surfactants and/or detergents. Undesirable non-specific adsorption of certain entities such as those listed above may be blocked by competitive non-specific adsorption of a blocking agent, e.g., by a protein such as bovine serum albumin (BSA) or immunoglobulin G (IgG). One may adsorb or covalently attach an assay reagent on an electrode and subsequently treat the electrode with a blocking agent so as to block remaining unoccupied sites on the surface.

In preferred embodiments, it may be desirable to immobilize (by either covalent or non-covalent means) biomolecules or other media to carbon-containing materials, e.g., carbon black, fibrils, and/or carbon dispersed in another material. One may attach antibodies, fragments of antibodies, proteins, enzymes, enzyme substrates, inhibitors, cofactors, antigens, haptens, lipoproteins, liposaccharides, cells, sub-cellular components, cell receptors, viruses, nucleic acids, antigens, lipids, glycoproteins, carbohydrates, peptides, amino acids, hormones, protein-binding ligands, pharmacological agents, and/or combinations thereof. It may also be desirable to attach non-biological entities such as, but not limited to polymers, elastomers, gels, coatings, ECL tags, redox active species (e.g., tripropylamine, oxalates), inorganic materials, chelating agents, linkers, etc. A plurality of species may be co-adsorbed to form a mixed layer on the surface of an electrode. Most preferably, biological materials (e.g., proteins) are immobilized on carbon-containing electrodes by passive adsorption. Surprisingly, biological membranes (e.g., cells, cell membranes, membrane fragments, membrane vesicles, liposomes, organelles, viruses, bacteria, etc.) may be directly adsorbed on carbon without destroying the activity of membrane components or their accessibility to binding reagents (see, e.g., copending U.S. application Ser. No. 10/208,526 (entitled "Assay Electrodes Having Immobilized Lipid/Protein Layers, Methods Of Making The Same And Methods Of Using The Same For Luminescence Test Measurements"), filed on Jul. 29, 2002, hereby incorporated by reference.

Electrodes used in the multi-well assay plates of the invention are typically non-porous, however, in some applications it is advantageous to use porous electrodes (e.g., mats of carbon fibers or fibrils, sintered metals, and metals films deposited on filtration membranes, papers or other porous substrates. These applications include those that employ filtration of solutions through the electrode so as to: i) increase mass transport to the electrode surface (e.g., to increase the kinetics of binding of molecules in solution to molecules on the electrode surface); ii) capture particles on the electrode surface; and/or iii) remove liquid from the well.

The assay modules of the present invention may use dielectric inks, films or other electrically insulating materials (hereinafter referred to as dielectrics). Dielectrics in the present invention may be used to prevent electrical connectivity between electrodes, to define patterned regions, to adhere materials together (i.e., as adhesives), to support materials, to define assay domains, as masks, as indicia and/or to contain assay reagents and other fluids. Dielectrics are non-conducting and advantageously non-porous (i.e., do not permit transmission of materials) and resistant to dissolving or degrading in the presence of media encountered in an electrode induced luminescence measurement. The dielectrics in the present invention may be liquids, gels, solids or materials dispersed in a matrix. They may be deposited in uncured form and cured to become solid. They may be inks, solid films, tapes or sheets. Materials used for dielectrics include polymers, photoresists, plastics, adhesives, gels, glasses, non-conducting inks, non-conducting pastes, ceramics, papers, elastomers, silicones, thermoplastics. Preferably, dielectric materials of the invention are substantially free of silicones. Examples of non-conducting inks include UV curable dielectrics such as materials produced by Acheson Colloids Co. (e.g., Acheson 451SS, 452SS, PF-021, ML25251, ML25240, ML25265, and Electrodag 38DJB16 clear) and E. I. du Pont de Nemours and Co. (e.g., Dupont: 5018, 3571, and 5017).

Dielectrics of the present invention may be applied by a variety of means, for example, printing, spraying, laminating, or may be affixed with adhesives, glues, solvents or by use of mechanical fasteners. Patterns and/or holes in dielectric layers may be formed by molding processes (i.e., during fabrication of the layer), by selective etching and/or by a cutting process such as die cutting or laser drilling. Dielectrics may be deposited and/or etched in patterns through the use of established photolithographic techniques (e.g., techniques used in the semiconductor electronics industry) and/or by patterned deposition using an evaporative or CVD process (e.g., by deposition through a mask). In a preferred embodiment, a dielectric ink is deposited on a substrate by printing (e.g., ink jet printing, laser printing or, more preferably, screen printing) and, optionally, UV cured. Preferably, the screen printed dielectric is UV curable allowing for improved edge definition than solvent based dielectrics. In another preferred embodiment, a non-conducting polymeric film is affixed to a support using an adhesive.

When using a dielectric ink printed on or adjacent an electrode to confine fluids to regions of the electrode surface, the dielectric film preferably has a thickness of 0.5-100 micrometers, or more preferably 2-30 micrometers, or most preferably 8-12 micrometers and also, preferably, has a sharply defined edge with steep walls.

The invention includes plate tops and assembled plates comprising a plate top and, preferably, a plate bottom defining well bottoms having one or more electrode surfaces, most preferably having one or more working electrode surfaces and, optionally, one or more counter electrode surfaces. Preferably, the plate top is a structure with holes, wherein the structure may be combined with a plate bottom to form a multi-well plate, the walls of the wells of the plate being at least partially defined by the inside surfaces of the holes through the plate top. The holes through the plate top may be a variety of shapes (e.g., round, oval, square, rectangular, triangular, star shaped, etc.). The holes may be of various sizes. They can also have irregular dimensions within a hole (e.g., the hole may become more narrow or more wide at different depths). For example, the hole may be shaped like a cone, becoming more narrow at the bottom so as to optimize the collection of light emitted from the well bottom. The plate top may also have structures or indicia thereon that aid in identifying the plate top, distinguishing the plate top from other configurations of plate top, or in aligning and handling the plate top. Advantageously, the dimensions and structure of the plate top are preferably in accordance with, or at least compatible with, industry standards for the footprints and shapes of assay plates.

The plate top may be made from conducting or non-conducting materials. Preferably, the majority of the plate top is a unitary molded structure made from rigid thermoplastic material such as polystyrene, polyethylene or polypropylene. Optimally, this unitary structure is formed of (or, alternatively, coated with) inexpensive material that is generally impervious to reactants, can withstand modest levels of heat and light and is, preferably, resistant to the adsorption of biomolecules. Preferably, the plate top is substantially free of silicones. Plate tops may be clear or translucent. Different colored materials may be used to improve the results of certain ECL measurement processes.

It is preferable that the plate top comprise a material that does not transmit light so as to prevent cross-talk between wells. A highly reflective metallic coating or constituent material may provide an especially reflective interior surface for each of wells so as to increase the efficiency with which light can be transmitted to photodetectors. An opaque white plastic material such as a plastic filled with light scattering particles (e.g., lead oxide, alumina, silica or, preferably, titanium dioxide particles) may provide an interior surface for the wells that is highly light scattering thereby improving light gathering efficiency. In one embodiment, preferred plate tops comprise plastics (e.g., well walls) comprising such light scattering particles at a concentration of from 4-20 wt %, preferably 6-20%, more preferably 6-15%, even more preferably 6-12%, and most preferred approximately 9%. In an alternate preferred embodiment, the plate top comprises an opaque, preferably non-reflective, black material to prevent the reflection or scattering of ECL-generated light from different locations within a well and to prevent reflective interference during ECL test measurements. In general, when imaging light emitted from a well (e.g., when using a camera to produce an image of light emitted from the well) it is advantageous that the interior surface of the well (e.g., as defined by a plate top) comprise an absorptive (e.g., black) preferably non-scattering material since the detection of scattered light will reduce the fidelity of the image. In general, when detecting light in a non-imaging mode (e.g., when a single light detector is used to detect all the light emitted from a well) it is advantageous that the interior surface of the well comprise a reflective or highly scattering material so as to prevent the loss of light due to adsorption of light at the well walls and to maximize the collection of light at the detector.

The invention also includes assay module tops and assembled assay modules comprising an assay module top and a plate bottom or assay module substrate. The assay module top may be a plate top (as described above). The assay module top may have, e.g., holes, channels, and/or wells that when mated to a plate bottom or assay module substrate define wells and/or chambers, such wells and/or chambers preferably comprising one or more electrodes (and/or assay domains) provided by the plate bottom or assay module substrate. The assay module top may have additional channels, tubes or other microfluidics so as to allow the flow of samples into, out of and/or between wells, flow cells and chambers of an assay module.

Figure 10A:
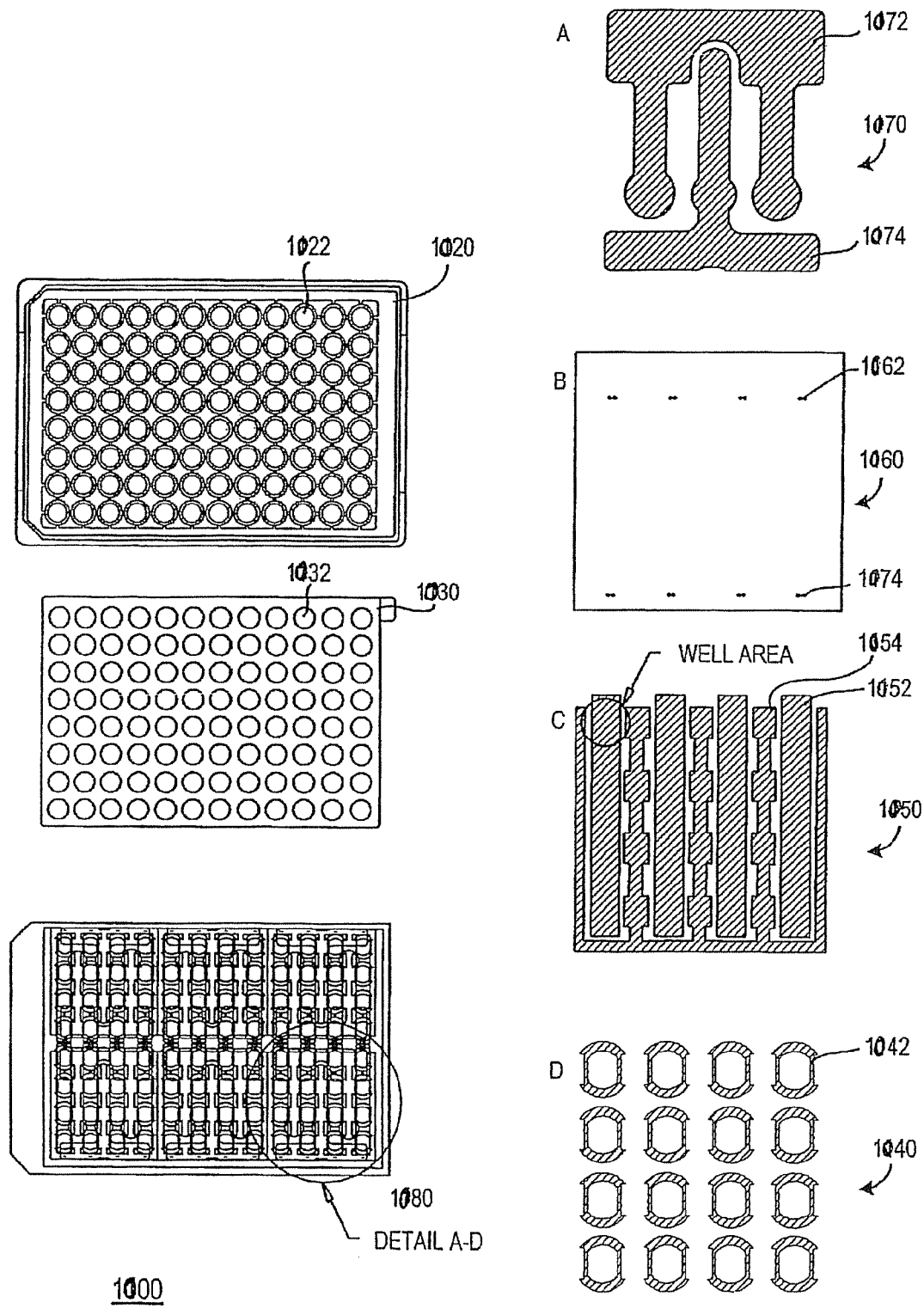
FIG. 10A shows a layered view of MDMW plate 1000, a MDMW plate that is adapted for electrode induced chemiluminescence measurements.
Figure 10B:
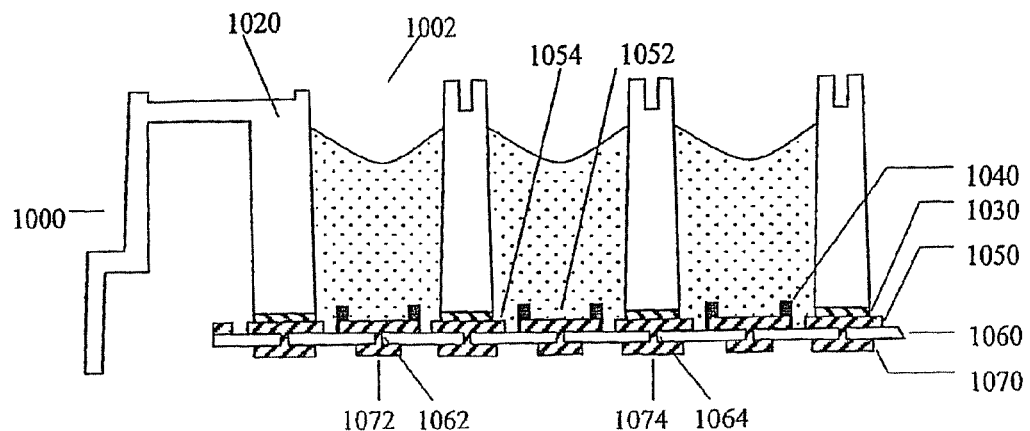
FIG. 10B shows a stylized cross sectional view of 3 wells of MDMW plate 1000, a MDMW plate that is adapted for electrode induced chemiluminescence measurements.

FIGS. 10A and 10B show a layered view and a stylized cross-sectional view, respectively, of an embodiment of the multi-well assay plate of the invention. Multi-well assay plate 1000 is a laminar structure comprising, in sequence, a plate top 1020, an adhesive layer 1030, a dielectric layer 1040, a conductive layer 1050, a substrate layer 1060 and a contact layer 1070. Holes 1022 and 1032 through plate top 1020 and adhesive layer 1030, respectively, are aligned so as to form a plurality of wells 1002 having well bottoms defined by dielectric layer 1040, conductive layer 1050 and/or substrate layer 1060 and well walls defined by the interior surfaces of holes 1022 and 1032. Through-holes 1062 and 1064 through substrate layer 1060 provide an electrical path between elements of conductive layer 1050 and elements of contact layer 1070. Details A-D show the pattern of layers 1070, 1060, 1050 and 1040 within a given sector of plate 1000. Element 1080 shows layers 1070, 1060, 1050 and 1040 aligned and stacked, in order from top to bottom—1040 (top), 1050, 1060, and 1070 (bottom)—so as to form a plate bottom with integrated electrodes.

Plate top 1020 is a plate top as described above. Adhesive layer 1030 is an adhesive suitable for forming a fluid-tight seal between plate top 1020 and dielectric layer 1040, conductive layer 1050 and/or substrate layer 1060. Adhesive layer 1030 may be an adhesive coating applied, e.g., by spray coating, onto plate top 1020. In a preferred embodiment, adhesive layer 1030 is a double sided adhesive tape (i.e., a plastic film coated on both sides with adhesive). Holes 1032 are preferably formed by a cutting process such as laser drilling or die cutting. Optionally, adhesive 1030 may be omitted (e.g., when the adjoining layers have adhesive properties or when sealing is accomplished without the use of adhesives, e.g., by clamping, heat sealing, sonic welding, solvent welding, etc.). Alternatively, both plate top 1020 and adhesive layer 1030 may be omitted.

Conductive layer 1050 comprises materials suitable for use as working electrodes and/or counter electrodes in an ECL assay and is supported on substrate 1060, a non-conductive substrate such as a plastic sheet or film. Preferably, conductive layer 1050 is a conductive coating such as a carbon ink and may be formed by a printing process such as screen printing. Conductive layer 1050 is sectioned, e.g., by screen printing in a defined pattern, into 6 electrically isolated working electrode sections 1052 and 6 electrically isolated counter electrode sections 1054 so as to divide plate 1000 into 6 independently addressable square sectors. As shown in the figure, the sectioning is designed so that fluid in a given well will be in contact with at least one working electrode section and at least one counter electrode section. The working electrode sections may have a different composition than the counter electrode sections so as to optimize the performance of the electrodes or they may comprise the same materials so as to minimize the complexity of manufacturing, e.g., to reduce the number of printing steps. Preferably, they both comprise a carbon ink overlayer over a silver ink underlayer; the carbon ink providing the active electrode surface and the silver ink providing sufficient conductivity so that, during use of the plate in an assay, electrical potential is evenly distributed throughout a particular section. When forming such layers, e.g., by a two step printing process, it is beneficial that the overlayer be of slightly larger dimensions than the underlayer and that it be of suitable thickness to ensure that a sample in wells 1002 is not exposed to the underlayer material. It may be beneficial to print or deposit the overlayer in multiple layers so as to ensure that the underlayer is completely covered so that the underlayer does not interfere with subsequent processing steps or with ECL measurements (e.g., a preferred electrode material comprises three layers of carbon ink over a layer of silver ink, the layers most preferably being deposited by screen printing). Dielectric layer 1040 is an electrically insulating film, preferably formed from a dielectric ink by a printing process such as screen printing. Dielectric layer 1040 is patterned so as to define the surfaces of conductive layer 1050 that contact fluids in wells 1002 (i.e., the surfaces that are not covered). Holes 1042 in dielectric layer 1040 define fluid containment regions on the working electrode sections 1052 of conductive layer 1050. In such fluid containment regions, the dielectric layer acts as a barrier that can be used to confine small volumes of fluids over the working electrode, e.g., to aid in depositing assay reagents onto selected assay domains within a well. Holes 1042 in dielectric layer 1040 define one fluid containment regions and/or assay domains on the working electrode surface within each well of plate 1000. Optionally, dielectric layer 1040 may be omitted (in such a case, reagents may still be deposited into defined assay domains by controlled deposition, e.g., using microdispensing or pin transfer techniques).

Contact layer 1070 is a conductive layer that allows for electrical connection of the multi-well assay plate to an external source of electrical energy. The contact layer is sectioned in a series of working electrode contacts 1072 and counter electrode contacts 1074 to allow independent connection to specific sections of electrodes 1052 and 1054. The contact layers are, preferably, formed by printing, most preferably screen printing, a silver ink under layer (to provide high conductivity) followed by a carbon ink overlayer (to prevent corrosion of the silver ink and prevent any deleterious effects by the exposed silver on a subsequent plasma processing step). Holes 1062 and 1064 in substrate 1060 are, preferably, made by a cutting process such as die cutting or laser drilling. Holes 1062 are filled with a conductive material to provide an electrical connection between working electrode contacts 1072 and working electrode sections 1052. Holes 1064 are filled with conductive material to provide an electrical connection between counter electrode contacts 1074 and counter electrode sections 1054. Holes 1062 and 1064 are preferably filled with conductive material during the formation of conductive layer 1050 or contact layer 1070, e.g., during the printing of a conductive ink on a substrate, excess ink is forced into holes in the substrate so as to fill the holes with the conductive ink.

In operation, test samples are introduced into wells of plate 1000. A source of electrical energy is connected across one or more working electrode sections 1052 and one or more counter electrode sections 1054 (via one or more of working electrode contacts 1072 and one or more of counter electrode contacts 1074, respectively). Application of electrical energy across these connections leads to the application of an electrochemical potential across the test samples via the exposed surfaces of electrode sections 1052 and 1054 (the application of electrochemical potential being confined to wells in sectors contacting working electrode and counter electrode sections that are in electrical connection to the source of electrical energy).

Figure 10C:
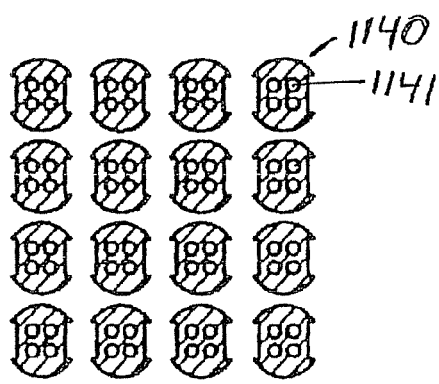
FIG. 10C shows dielectric layer 1140, a modification of dielectric layer 1040 shown in FIGS. 10A and 10B.
Figure 10D:
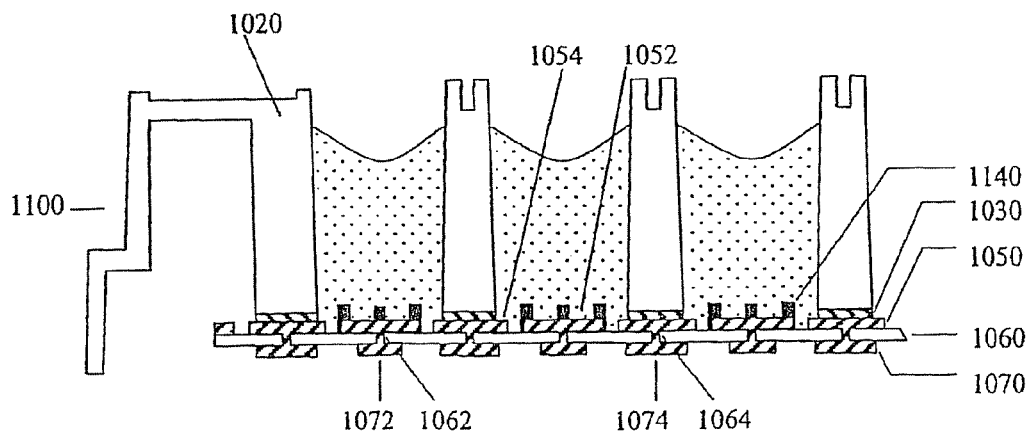
FIG. 10D shows a stylized cross-sectional view of 3 wells of MDMW plate 1100, a modification of plate 1000 employing dielectric layer 1140

The structure shown in FIGS. 10A and 10B is readily modified so as to be applicable to plates having different numbers of wells, different arrangements of wells and/or different arrangements of independently addressable sectors. Preferred embodiments include 96-well plates having 4, 7, or 10 assay domains per well and 24-well plates having 25, 64 or 100 wells per plate. FIG. 10C shows dielectric layer 1140, a modification of dielectric layer 1040 designed to expose 4 "fluid containment regions" 1141 on the working electrode surface of each well (the figure is only shown for one sector of the plate). FIG. 10D shows a stylized cross-sectional view of 3 wells of plate 1100 which is identical to plate 1000 except for the replacement of dielectric layer 1040 with dielectric layer 1140.

Figure 11:
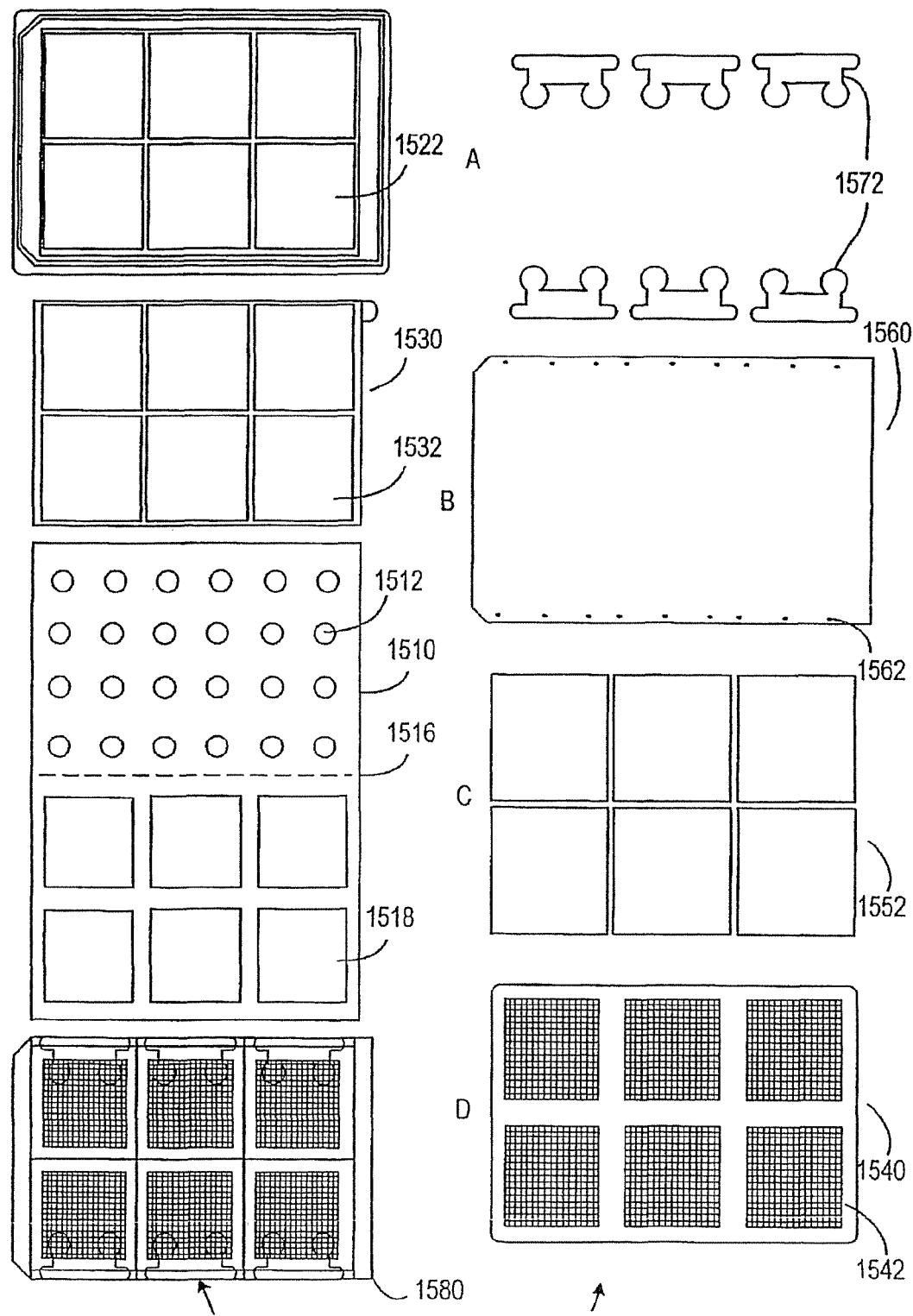
FIG. 11 shows a view of a MDMW plate adapted for electrode induced chemiluminescence measurements.

FIG. 11 shows, multi-well assay plate 1500, an embodiment of the invention that is particularly well suited for genomic or proteomic analysis. The size of the wells is chosen so as to optimize the efficiency of the imaging of luminescence generated from the wells by the imaging instrument (as described below). Multi-well assay plate 1500 is a laminar structure comprising, in sequence, plate top 1520, adhesive layer 1530, conductive tape layer 1514B, dielectric layer 1540, conductive layer 1552, substrate 1560, contact layer 1572 and conductive tape layer 1514A. Element 1580 shows layers 1572, 1560, 1552 and 1540 aligned and stacked, in order from top to bottom, 1540 (top), 1552, 1560, 1572 (bottom). Conductive tape layers 1514A and 1514B are provided by folding conductive tape 1510 around element 1580 at fold 1516. Holes 1522, 1532 and 1518 are aligned so as to form a plurality of wells having well bottoms defined by element 1580. Through-holes 1562 through substrate 1560 provide an electrical path between conductive layer 1552 and contact layer 1572. Through holes 1512 through conductive tape layer 1514A provide access to contact layer 1572 (and, therefore a way to contact conductive layer 1552). Plate top 1520 is analogous to plate top 1020 from FIG. 10 except for the specific arrangement of wells. Adhesive layer 1530 is an adhesive analogous to adhesive layer 1030 in FIG. 10 and may be omitted. Conductive tape 1510 is a laminate structure comprising a conductive film on an insulating and adhesive substrate (preferably, a plastic film coated on one side with an evaporated layer of aluminum and on the other side with an adhesive). Substrate 1560, conductive layer 1552, dielectric layer 1540 and contact layer 1572 are similar in composition and preparation to substrate 1060, conductive layer 1050, dielectric layer 1040 and contact layer 1072 as described for FIG. 10. Conductive layer 1552 is sectioned into 6 square sections so as to divide plate 1500 into 6 independently addressable sectors (each having one well). Holes 1542 through dielectric layer 1540, define a large number (preferably 10-50,000, more preferably 100-10,000; 256 are shown in the figure) of fluid containment regions in each well. Binding reagents such as specific nucleic acid sequences or specific proteins can be selectively introduced and or immobilized into specific fluid containment regions by selectively microdispensing the binding reagents into the specific fluid containment regions.

While the figures illustrating embodiments of the plates of the invention have shown specific patterns for number, shape and distribution of wells, sectors and fluid containment regions/assay domains, it should be clear that the designs are adaptable so as to allow for a wide variation in these parameters.

The assay domains and immobilized layers of the invention are useful for carrying out a wide variety of established assay formats, e.g., assays based on the measurement of electrochemical voltage and/or current or, preferably, an electrode-induced luminescence, most preferably, electrochemiluminescence. For examples of methods for conducting ECL assays, the reader is directed towards U.S. Pat. Nos. 5,591,581; 5,641,623; 5,643,713; 5,705,402; 6,066,448; 6,165,708; 6,207,369; and 6,214,552 and Published PCT Applications WO87/06706 and WO98/12539, these references hereby incorporated by reference. Assays may be directed to, but are not limited to, the measurement of the quantity of an analyte; the measurement of a property of a sample (e.g., temperature, luminescence, electrochemical activity, color, turbidity, etc.); the measurement of a chemical, biochemical and/or biological activity (e.g., an enzymatic activity); the measurement of a kinetic or thermodynamic parameter (e.g., the rate or equilibrium constant for a reaction), etc.

The embodiments of the invention can be used to test a variety of samples which may contain an analyte or activity of interest. Such samples may be in solid, emulsion, suspension, liquid, or gas form. They may be, but are not limited to, samples containing or derived from, for example, cells (live or dead) and cell-derived products, cell fragments, cell fractions, cell lysates, organelles, cell membranes, cell culture supernatants (including supernatants from antibody producing organisms such as hybridomas), waste or drinking water, food, beverages, pharmaceutical compositions, blood, serum, plasma, hair, sweat, urine, feces, tissue, saliva, mucous, oils, sewage, environmental samples, organic solvents or air. The sample may further comprise, for example, water, organic solvents (e.g., acetonitrile, dimethyl sulfoxide, dimethyl formamide, n-methyl-pyrrolidone or alcohols) or mixtures thereof.

Analytes that may be measured include, but are not limited to, whole cells, cell surface antigens, subcellular particles (e.g., organelles or membrane fragments), viruses, prions, dust mites or fragments thereof, viroids, antibodies, antigens, haptens, fatty acids, nucleic acids (and synthetic analogs), proteins (and synthetic analogs), lipoproteins, polysaccharides, inhibitors, cofactors, haptens, cell receptors, receptor ligands, lipopolysaccharides, glycoproteins, peptides, polypeptides, enzymes, enzyme substrates, enzyme products, second messengers, cellular metabolites, hormones, pharmacological agents, synthetic organic molecules, organometallic molecules, tranquilizers, barbiturates, alkaloids, steroids, vitamins, amino acids, sugars, lectins, recombinant or derived proteins, biotin, avidin, streptavidin, or inorganic molecules present in the sample. Activities that may be measured include, but are not limited to, the activities of phosphorylases, phosphatases, esterases, trans-glutaminases, nucleic acid damaging activities, transferases, oxidases, reductases, dehydrogenases, glycosidases, ribosomes, protein processing enzymes (e.g., proteases, kinases, protein phosphatases, ubiquitin-protein ligases, etc.), nucleic acid processing enzymes (e.g., polymerases, nucleases, integrases, ligases, helicases, telomerases, etc.), cellular receptor activation, second messenger system activation, etc.

In one embodiment of the invention, a sample potentially containing a luminescent, chemiluminescent and/or redox-active substance (preferably an ECL-active substance) is introduced to an assay plate or one or more wells of an assay plate of the invention and an electrochemical or luminescent signal (preferably, electrochemiluminescence) from the sample is induced and measured from one or more assay domains so as to measure the quantity of the substance and/or identify the substance. In another embodiment of the invention, a sample containing a luminescent, chemiluminescent and/or redox-active substance (preferably an ECL-active substance) is introduced to an assay plate or one or more wells of an assay plate of the invention and an electrochemical or luminescent signal (preferably, electrochemiluminescence) from the sample is induced and measured from one or more assay domains so as to measure the presence of substances, chemical activities or biological activities that affect the production of the signal from the substance (e.g., the presence, production and/or consumption of ECL coreactants, hydrogen ions, luminescence quenchers, chemiluminescence triggers, etc.). In other embodiments of the invention, luminescent, chemiluminescent and/or redox-active substances (preferably ECL-active substances) are used as labels to allow the monitoring of assay reagents such as enzyme substrates or binding reagents. Assay formats for measuring analytes through the use of labeled binding reagents specific for the analyte include homogeneous and heterogeneous methods. Heterogeneous methods may include a wash step to separate labels (and/or labels attached to a material) on a solid phase/electrode from labels in solution.

A wide variety of materials have been shown to emit electrode induced luminescence, particularly electrochemiluminescence, and may be used with the methods, plates, kits, systems and instruments of the invention. In preferred electrochemiluminescence systems, ECL-active materials and/or labels are regenerated after the emission of electrochemiluminescence and, during an electrochemiluminescence experiment, may be repeatedly excited to an excited state and/or induced to emit luminescence. For example, one class of ECL-active materials are believed to function via a mechanism that includes the steps of i) oxidation of the material; ii) reduction of the oxidized material by a strong reducing agent so as to produce the material in an excited state and iii) emission of a photon from the excited state so as to regenerate the ECL-active material. Preferably, the difference in redox potentials between the ECL-active material and the strong reducing agent is sufficient so that the energy released by step (ii) is equal to or greater than the energy of the photon. In an analogous mechanism, steps (i) and (ii) may be replaced by i) reduction of the material and ii) oxidation of the reduced material by a strong oxidizing agent. In some especially preferred systems, the mechanism is believed to further comprise the step of oxidizing an ECL coreactant so as to form the strong reducing agent or, analogously, reducing an ECL coreactant to form the strong oxidizing agent.

Preferred luminescent materials and labels include luminescent organometallic complexes of Ru, Os and Re. Some especially useful materials are polypyridyl complexes of ruthenium and osmium, in particular, complexes having the structure $ML^1L^2L^3$ where M is ruthenium or osmium, and $L^1$, $L^2$ and $L^3$ each are bipyridine, phenanthroline, substituted bipyridine and/or substituted phenanthroline. We have found that the inclusion of substituted bipyridines or phenanthrolines presenting substituents comprising negatively charged groups, preferably sulfate groups and most preferably sulfonate groups (as described in copending U.S. patent application Ser. No. 09/896,974, entitled "ECL Labels Having Improved Non-Specific Binding Properties, Methods of Using and Kits Containing the Same" filed Jun. 29, 2001, the disclosure hereby incorporated by reference) are especially preferred due to their resistance to non-specific binding, in particular to electrodes comprising carbon, carbon particles, carbon fibrils, carbon composites, carbon fibril composites and/or carbon inks.

The invention also relates to detection methods using the electrodes of the present invention.

One aspect of the invention relates to methods of measuring an analyte of interest, wherein the analyte of interest is immobilized on an electrode (preferably in an assay domain of an assay cell or assay well). One embodiment comprises the steps of: i) immobilizing the analyte of interest on an electrode, preferably within an assay domain, e.g., by contacting the electrode with a sample comprising the analyte of interest and ii) measuring the analyte of interest. The immobilization preferably proceeds via the formation of covalent bonds to functional groups on the electrode, or more preferably via the formation of specific binding interactions with binding reagents immobilized on the electrode, or most preferably via passive adsorption on the electrode.

Another aspect of the invention relates to methods of measuring an analyte of interest that binds to a biomaterial, wherein the biomaterial is immobilized on an electrode (preferably in an assay domain of an assay cell or assay well). One embodiment comprises the steps of i) contacting the biomaterial with a sample comprising the analyte; ii) forming a complex on the electrode comprising the analyte and the biomaterial and ii) measuring the analyte of interest. The biomaterial is preferably immobilized on the electrode via covalent bonds to functional groups on the electrode, or more preferably via specific binding interactions with a capture reagent immobilized on the electrode, or most preferably via passive adsorption on the electrode. Optionally, the assay method also comprises the step of immobilizing the biomaterial on the electrode. This immobilization step can be carried out before, during and/or after the step of contacting the biomaterial with the sample.

Preferably, the aforementioned methods of measuring an analyte further comprise the steps of applying electrical energy (e.g., current or voltage) to the electrode (preferably, under conditions appropriate for inducing electrochemiluminescence, e.g., in the presence of an ECL coreactant) and measuring luminescence (preferably, electrochemiluminescence) induced at the electrode (e.g., from a luminescent species, preferably an electrochemiluminescent species, associated with the analyte), wherein the luminescence signal correlates to the amount of analyte present. Optionally, the method may comprise the step of introducing an ECL coreactant prior to the induction of luminescence. The luminescent species may be the analyte itself or it may be a luminescent species linked to the analyte. Such linkages may include i) a covalent bond, ii) a specific binding interaction (e.g., via a labeled antibody directed against the analyte) and/or iii) a non-specific binding interaction. The assay method, preferably, further comprises the step of forming the linkage between the label and the analyte, e.g., by contacting or mixing the analyte with a label or a labeled reagent such as a labeled binding reagent. The formation of the linkage may be carried out before, during and/or after the immobilization step. The assay method may also include one or more wash steps to remove material (e.g., analyte, biomaterial, blocking reagent, labeled reagent, etc.) that is not bound to the electrode.

Another aspect of the invention relates to methods of measuring a binding interaction of a biomaterial with a binding partner, wherein the biomaterial is immobilized on an electrode (preferably in an assay domain of an assay cell or assay well). One embodiment comprises the steps of i) contacting the biomaterial with a binding partner of the biomaterial; ii) forming a complex on the electrode comprising the biomaterial and the binding partner and ii) measuring the complex so as to measure the binding interaction. The biomaterial is preferably immobilized on the electrode via covalent bonds to functional groups on the electrode, or more preferably via specific binding interactions with a capture reagent immobilized on the electrode, or most preferably via passive adsorption on the electrode. Optionally, the assay method also comprises the step of immobilizing the biomaterial on the electrode. This immobilization step can be carried out before, during and/or after the step of contacting the biomaterial with the binding partner. The measurement of the binding interaction may be used in a variety of applications including, but not limited to, i) measuring the amount of the biomaterial; ii) measuring the amount of the binding partner and iii) measuring the affinity of a biomaterial for binding partner. The assay method may further comprise the step of contacting the biomaterial and/or the binding partner with an inhibitor of the binding interaction so that the extent of binding is indicative, e.g., of the amount of the inhibitor or the inhibition constant of the inhibitor. The inhibition assay may also be used to screen compounds for inhibitors of the binding interaction.

Preferably, the aforementioned method of measuring a binding interaction further comprises the steps of applying electrical energy (e.g., current or voltage) to the electrode (preferably, under conditions appropriate for inducing electrochemiluminescence, e.g., in the presence of an ECL coreactant) and measuring luminescence (preferably, electrochemiluminescence) induced at the electrode (e.g., from a luminescent species, preferably an electrochemiluminescent species, associated with the binding partner), wherein the luminescence signal correlates to the number of binding interactions. Optionally, the method may comprise the step of introducing an ECL coreactant prior to the induction of luminescence. The luminescent species may be the binding partner itself or it may be a luminescent species linked to the binding partner. Such linkages may include i) a covalent bond, ii) a specific binding interaction (e.g., via a labeled antibody directed against the binding partner) and/or iii) a non-specific binding interaction. The assay method, preferably, further comprises the step of forming the linkage between the label and the binding partner, e.g., by contacting or mixing the binding partner with a label or a labeled reagent such as a labeled binding reagent. The formation of the linkage may be carried out before, during and/or after the immobilization step. The assay method may also include one or more wash steps to remove material (e.g., binding partner, biomaterial, blocking reagent, labeled reagent, etc.) that is not bound to the electrode.

Another aspect of the invention relates to methods of measuring an activity or process that modifies a substance, the method comprising the steps of subjecting the substance to a sample comprising the activity or to conditions under which the process occurs and measuring the extent of the modification so as to measure the activity or process. The extent of the modification is, preferably, measured by selectively measuring the modified substance and/or the remaining unmodified substance according to the assay methods of the invention (e.g., by using labeled antibodies specific for the starting material or product). Optionally, the activity or process is carried out in the presence of an inhibitor of the activity or process so that the extent of modification is indicative, e.g., of the amount of the inhibitor or the inhibition constant of the inhibitor. The inhibition assay may also be used to screen compounds for inhibitors of the binding interaction and/or for measuring an activity or process that modifies a binding partner of an immobilized substance.

In one embodiment, a substance is immobilized on an electrode (preferably in an assay domain of an assay cell or assay well) and subjected to a modifying activity or process, and assayed to determine the extent of modification. In another embodiment, a substance is subjected to a modifying activity or process, immobilized on an electrode, and assayed to determine the extent of modification. In yet another embodiment, a cell is subjected to a modifying activity or process, the cell is lysed, a biological membrane or other component derived from the cell (e.g., an protein, nucleic acid, second messenger, organelle, membrane fragment, membrane vesicle, membrane ghost, membrane protein, membrane lipid, etc) is immobilized on an electrode, and assayed to determine the extent of modification. Examples of activities and processes that can be measured include kinase activity/phosphorylation (including autophosphorylation of membrane bound kinases), phosphatase activity/dephosphorylation, changes in membrane lipid composition or orientation (e.g., changes in phosphatidyl serine levels during apoptosis), hydrolysis or changes in phosphorylation state of membrane phosphatidyl inositols, prenylation or myristoylation of proteins, binding and/or release of soluble proteins and/or peripheral membrane proteins to biological membranes, transfer of proteins and/or lipids between biological membranes (e.g., between organelles and/or between an organelle and the cytoplasmic membrane), etc.

One embodiment of the method of measuring an activity or process (or, alternatively, an inhibitor of an activity or process) that modifies a substance relates to measuring an activity or process that results from the activation of a membrane protein (e.g., as a result of a change in the physical or chemical environment, a change in membrane potential, the aggregation of the protein, the binding of a ligand to a membrane receptor, etc.). For example, the activation of a membrane protein may lead to phosphorylation of the protein or of other components of the membrane (the phosphorylated components being measured, e.g., using phosphopeptide specific antibodies); ii) the sequestration or binding (or, alternatively, the release) to the membrane of soluble cellular components such as peripheral membrane proteins or cytoplasmic proteins (the binding of soluble cellular components being measured, e.g., using antibodies specific for the components); iii) the up or down regulation of membrane proteins (the membrane proteins being measured, e.g., using antibodies specific for the specific membrane protein being monitored), etc.

Another aspect of the invention relates to kits for use in conducting assays, preferably luminescence assays, more preferably electrode induced luminescence assays, and most preferably electrochemiluminescence assays, comprising an assay module, preferably an assay plate, more preferably a multi-well assay plate, and at least one assay component selected from the group consisting of binding reagents, enzymes, enzyme substrates and other reagents useful in carrying out an assay. Examples include, but are not limited to, whole cells, cell surface antigens, subcellular particles (e.g., organelles or membrane fragments), viruses, prions, dust mites or fragments thereof, viroids, antibodies, antigens, haptens, fatty acids, nucleic acids (and synthetic analogs), proteins (and synthetic analogs), lipoproteins, polysaccharides, lipopolysaccharides, glycoproteins, peptides, polypeptides, enzymes (e.g., phosphorylases, phosphatases, esterases, trans-glutaminases, transferases, oxidases, reductases, dehydrogenases, glycosidases, protein processing enzymes (e.g., proteases, kinases, protein phosphatases, ubiquitin-protein ligases, etc.), nucleic acid processing enzymes (e.g., polymerases, nucleases, integrases, ligases, helicases, telomerases, etc.)), enzyme substrates (e.g., substrates of the enzymes listed above), second messengers, cellular metabolites, hormones, pharmacological agents, tranquilizers, barbiturates, alkaloids, steroids, vitamins, amino acids, sugars, lectins, recombinant or derived proteins, biotin, avidin, streptavidin, luminescent labels (preferably electrochemiluminescent labels), electrochemiluminescence coreactants, pH buffers, blocking agents, preservatives, stabilizing agents, detergents, dessicants, hygroscopic agents, etc. Such assay reagents may be unlabeled or labeled (preferably with a luminescent label, most preferably with an electrochemiluminescent label). One embodiment of the invention includes a kit for use in conducting assays, preferably luminescence assays, more preferably electrode induced luminescence assays, and most preferably electrochemiluminescence assays, comprising an assay module, preferably an assay plate, more preferably a multi-well assay plate, and at least one assay component selected from the group consisting of: (a) at least one luminescent label (preferably electrochemiluminescent label); (b) at least one electrochemiluminescence coreactant); (c) one or more binding reagents; (d) a pH buffer; (e) one or more blocking reagents; (f) preservatives; (g) stabilizing agents; (h) enzymes; (i) detergents; (j) desiccants and (k) hygroscopic agents.

Preferably, the kit comprises the assay module, preferably an assay plate, and the assay component(s) in one or more, preferably two or more, more preferably three or more containers.

Preferably, the assay module is a multi-well plate is adapted for use in conducting the electrode induced luminescence assays (preferably electrochemiluminescence assays) in sectors.

According to one embodiment, the kit comprises one or more of the assay components in one or more plate wells, preferably in dry form.

According to one embodiment, the assay components are in separate containers. According to another embodiment, the kit includes a container comprising binding reagents and stabilizing agents. According to another embodiment, the well reagents may include binding reagents, stabilizing agents. Preferably, the kits do not contain any liquids in the wells.

One preferred embodiment relates to a kit for use in conducting electrode induced luminescence assays (preferably electrochemiluminescence assays) comprising an assay plate, preferably a multi-well assay plate, and at least one assay component selected from the group consisting of at least one luminescent label (preferably electrochemiluminescent label) and at least one electrochemiluminescence coreactant).

Another embodiment relates to a kit comprising a multi-well plate and at least one electrode induced luminescent label (preferably electrochemiluminescent label) and/or at least one bioreagent and/or at least one blocking reagent (e.g., BSA).

According to one preferred embodiment, the kit comprises at least one bioreagent, preferably immobilized on the plate surface selected from: antibodies, fragments of antibodies, proteins, enzymes, enzyme substrates, inhibitors, cofactors, antigens, haptens, lipoproteins, liposaccharides, cells, subcellular components, cell receptors, viruses, nucleic acids, antigens, lipids, glycoproteins, carbohydrates, peptides, amino acids, hormones, protein-binding ligands, pharmacological agents, luminescent labels (preferably ECL labels) or combinations thereof.

According to another preferred embodiment, the kit comprises at least one biological membrane or component thereof, preferably immobilized on the plate surface, that comprises an active protein selected from: single transmembrane receptors with intrinsic tyrosine kinase activity; non-tyrosine kinase transmembrane receptors (e.g., transferrin receptor); G-protein coupled receptors (GPCR); GPCR effector proteins (e.g., adenylate cyclase); phosphoinositides (e.g., phosphatidy inositol 4,5 bisphosphate ($PIP_2$)); phospholipid or sphingolipid composition, identification, or function (i.e., changes in phosphotidylserine presence during apoptosis); organelle-bound GTPases/guanine nucleotide exchange factors (GEFs)/GTPase activating proteins (GAPs); cytokine/chemokine receptors; cell adhesion molecules (e.g., VCAM, integrins); cytoplasmic peripheral membrane protein kinases (e.g., src); intracellular protein kinase adaptor/docking proteins (e.g., insulin receptor substrate 1, GRB2); ion channels (e.g., nicotinic acetylcholine receptor, CFTR, etc.); passive transporters (e.g., glucose); active (ATP-driven) transporters; ion-linked transporters (e.g., Na+/glucose); glycosyltransferases/glycoprotein modifying enzymes; nuclear membrane fragments; and soluble receptors.

Preferably, the kit includes immobilized reagents comprised of proteins, nucleic acids, or combinations thereof.

According to one preferred embodiment, the plurality of wells includes at least two different bioreagents. For example, a well may include two or more assay domains, wherein two or more assay domains have different bioreagents.

Preferably, the kit comprises at least one electrochemiluminescence coreactant and/or at least one electrode induced luminescence label (preferably electrochemiluminescent label).

Another aspect of the invention relates to improved methods and systems for selecting or identifying biologically active compounds and, optionally, incorporating such biologically active compounds into suitable carrier compositions in appropriate dosages. The invention includes the use of the assay electrodes, kits and/or methods of the invention to screen for new drugs, preferably, by high-throughput screening (HTS), preferably involving screening of greater than 50, more preferably 100, more preferably 500, even more preferably 1,000, and most preferably 5,000. According to a particularly preferred embodiment, the screening involves greater than 10,000, greater than 50,000, greater than 100,00, greater than 500,000 and/or greater than 1,000,000 compounds.

One embodiment of the invention relates to a method for selecting or identifying biologically active compounds from a library of compounds, said method comprising screening said library of compounds for biological or biochemical activity, wherein said screening includes assaying the library of compounds for the biological or biochemical activity, the assays being conducted using the assay electrodes of the invention.

Preferably, the method further comprises identifying one or more active compounds.

Preferably, the method further comprises testing said one or more active compounds for bioavailability, toxicity and/or biological activity in vivo. According to one preferred embodiment, the testing comprises further screening using the assay electrodes of the invention.

Preferably, the method further comprises synthesizing analogues of said one or more active compounds. According to one preferred embodiment, the analogues are screened for bioavailability, biological activity and/or toxicity using the assay electrodes of the invention.

According to a particularly preferred embodiment, the method further comprises formulating the one or more compounds into drugs for administrating to humans and/or animals.

Preferably, the formulating comprises determining the suitable amount of the one or more active compounds in the drug and mixing the suitable amount with one or excipients or carriers. Preferably, the excipient comprises sugar and/or starch.

Another embodiment of the invention relates to a method of analyzing one or more complex mixtures of biochemical substances to measure a plurality of binding components therein, comprising:
(a) contacting said mixtures with one or more assay electrodes having one or more lipid/protein layers immobilized thereon, preferably by adding said mixtures to a multi-well plate adapted for electrode induced luminescence assays (preferably electrochemiluminescence assays), wherein the wells of the plate include the assay electrodes;
(b) applying a voltage or current to the electrodes sufficient to induce luminescence; and
(c) measuring emitted luminescence.

Another embodiment of the invention relates to a method of analyzing the output of one or more combinatorial (biological and/or chemical) mixtures to measure a plurality of binding components therein, comprising:
(a) contacting said mixtures to one or more assay electrodes, preferably by introducing said mixture into a multi-well plate adapted for electrode induced luminescence (preferably electrochemiluminescence) assays, said plate having a plurality of wells comprising one or more assay electrodes;
(b) applying a voltage or current to the electrodes sufficient to induce luminescence; and
(c) measuring emitted luminescence.

Another embodiment of the invention relates to a method for measuring a single biochemical substance in a sample in a multiplicity of simultaneous assays, comprising:
(a) contacting said sample with an assay electrode, preferably by introducing said sample into a multi-well plate adapted for electrode induced luminescence (preferably electrochemiluminescence) assays, said plate having a plurality of wells comprising one or more assay electrodes;
(b) applying a voltage or current to the electrodes sufficient to induce luminescence; and
(c) measuring emitted luminescence.

A further embodiment of the invention relates to a method of drug discovery comprising:
(a) selecting a multiplicity of compounds for testing;
(b) screening said multiplicity of compounds for biological activity (using any one of the multi-well plates and/or apparatus described above) to find one or more biologically active compounds; and
(c) modifying said one or more biologically active compounds to reduce toxicity and/or enhance biological activity thereby forming one or more modified biologically active compounds.

Preferably, the method further comprises screening said modified biologically active compounds for biological activity and/or toxicity (using the assay electrodes of the invention described above).

Preferably, the method further comprises determining the appropriate dosage of one or more of said modified biologically active compounds. Preferably, the method still further comprises incorporating such dosage into a suitable carrier such as sugar or starch to form a drug in solid (e.g., pill or tablet) or liquid form.

Advantageously, the assay electrodes, assay modules and methods of the invention may be integrated into and/or used in a variety of screening and/or drug discovery methods. Such screening and/or drug discovery methods include those set forth in U.S. Pat. No. 5,565,325 to Blake; U.S. Pat. No.

5,593,135 to Chen et al.; U.S. Pat. No. 5,521,135 to Thastrup et al.; U.S. Pat. No. 5,684,711 to Agrafiotis et al.; U.S. Pat. No. 5,639,603 to Dower et al.; U.S. Pat. No. 5,569,588 to Ashby et al.; U.S. Pat. No. 5,541,061; U.S. Pat. No. 5,574,656; and U.S. Pat. No. 5,783,431 to Peterson et al.

According to another embodiment, the invention further comprises identifying adverse effects associated with the drug and storing information relating to the adverse effects in a database. See, U.S. Pat. No. 6,219,674 by Classen, hereby incorporated by reference.

Another aspect of the invention relates to improved biologically active compounds and/or drugs made using the inventive methods.

6. EXAMPLES

The following examples are illustrative of some of the electrodes, plates, kits and methods falling within the scope of the present invention. They are, of course, not to be considered in any way limitative of the invention. Numerous changes and modification can be made with respect to the invention by one of ordinary skill in the art without undue experimentation.

Example 1

Fabrication of Multi-Well Assay Plates Having Screen Printed Electrodes

Multi-layer plate bottoms were prepared by screen printing electrodes and electrical contacts on 0.007" thick Mylar polyester sheet. The Mylar sheet was first cut with a $CO_2$ laser so to form conductive through-holes (i.e., holes that were subsequently made conductive by filling with conductive ink) as well as to form alignment holes that were used to align the plate bottom with the plate top. Electrical contacts were formed on the bottom of the Mylar sheet by screen printing an appropriately patterned silver ink layer (Acheson 479ss) and a carbon ink overlayer (Acheson 407c). The carbon ink layer was dimensioned slightly larger (0.01 inches) than the silver ink layer to prevent exposure of the edge of the silver film. Working and counter electrodes were formed on the top of the Mylar film in a similar fashion except that three layers of carbon ink were used to ensure that no silver remained exposed. The conductive through-holes filled with conductive ink during these screen-printing steps. A dielectric ink was subsequently printed over the electrode layers so as to define the active exposed surface area of the working electrode. Typically, nine plate bottoms were simultaneously printed on an 18"×12" Mylar sheet. Typical registrational tolerances during the screen printing steps were +/−0.007-0.008 inches on the top side of the substrate and +/−0.010 inches on the bottom side. The separation between the printed counter and working electrode strips was kept at >0.010 inches to prevent the formation of short circuits. Optionally, the working electrodes were conditioned by treating the patterned plate bottoms for 5 min. with an oxygen plasma (2000 W, 200 mtorr) in a plasma chamber (Series B, Advanced Plasma Systems, St. Petersburg, Fla.) modified with large area flat electrodes.

Multi-well assay plates were assembled using the plate bottoms described above and injection molded plate tops. The dimensions of the plate tops met industry standards as established by the Society of Biomolecular Screening. The plate tops were either made of black plastic (polystyrene loaded with black pigment) or white plastic (polystyrene loaded with titanium dioxide). The bottom surfaces of the plate tops were contacted with die-cut double sided tape (1 mil PET coated on each side with 2 mil of acrylic pressure sensitive adhesive) so as to allow for sealing of the plate tops to the plate bottoms. The tape was cut to form holes that were slightly oversized relative to the holes in the plate tops. The plate bottoms were fixed (using the laser cut alignment holes) onto alignment pins on an X-Y table. The plate bottoms were optically aligned to the plate tops and then sealed together using a pneumatic press (400 pounds, 10 s). Alignment was carried out sufficiently accurately so that the exposed working electrodes were centered within the wells (+/−0.020 inches for 96-well plates and +/−0.015 inches for 384 well plates). These tolerances ensured that the exposed regions of the working electrodes were within the wells and that there were exposed counter electrode surfaces on both sides of the working electrode. In some examples, assay reagents were deposited and dried on the plate bottoms prior to assembly of the plate.

A variety of types of multi-well assay plates were prepared according to the procedure described above. A few specific plate designs are described in more detail below to allow for reference in subsequent examples. Plate B, a 96-well plate sectioned into 6 square sectors of 4×4 wells, was prepared using components and patterns as pictured in FIG. 10A and had a black plate top. Plate C, a 96-well plate sectioned into 6 square sectors of 4×4 wells, was prepared using components and patterns as pictured in FIG. 10 (except that the dielectric layer in Plate C is patterned so as to expose four isolated "fluid containment regions" on the working electrode surface within each well, see FIGS. 10C and 10D) and a black plate top. Plate D was similar to Plate C except that the dielectric layer was patterned so as to expose 7 isolated "fluid containment regions" on the working electrode within each well. Plate E was similar to Plate C except that the dielectric layer was patterned so as to expose 10 isolated "fluid containment regions" on the working electrode within each well. Plate F, G and H were analogous to Plate C, except that they had 24 wells that were square in shape (the plates being sectored into 6 square sectors of 4 wells) and the dielectric layer was patterned to expose 25, 64 or 100 fluid containment regions, respectively. In FIG. 10A, details A, B, C and D show for Plate B: the printed contact layer, the Mylar film with through-holes, the printed electrode layer and the printed dielectric layer (in one sector of the plate), respectively.

Example 2

ECL Measurements

Plates were read on an instrument designed to make electrical contact to individual square sectors. The sector in electrical contact with the instrument was aligned with a telecentric lens (having a front element with a diameter of 4.1") coupled to a cooled CCD camera (VersArray: 1300F, Princeton Instruments) that was used to image ECL emitted from the sector. The camera employed a CCD chip with dimensions of roughly 2.6 cm×2.6 cm and having a 1340×1300 array of pixels. The pixel size was 0.02 mm×0.022 mm. An optical band pass filter in the optical path was used to select for light matching the emission profile of ruthenium-tris-bipyridine. A translation table was used to translate the plate under the telecentric lens so as to allow all 6 sectors to be read. Image analysis software was used to identify wells or assay domains within wells and to quantitate ECL from specific wells or domains. ECL from plates having screen printed carbon working electrodes was induced using a linear voltage scan from roughly 2-5 V over 3 seconds unless otherwise indicated. ECL is reported as the total integrated light signal measured over the period of the voltage scan (after correcting for background light levels and detector offset).

Example 3

An ECL Assay Measuring Multiple Activities of an Enzyme in One Well of an MDMW Plate Many nucleic acid processing enzymes have both nucleic acid synthesizing (e.g., polymerase or ligase) activities and nuclease activities. One example is HIV Reverse Transcriptase (RT), an enzyme with both a RNA-dependent DNA polymerase (RDDP) activity and an RNAse H activity. The following example demonstrates an ECL assay for measuring both HIV RT activities in one well of an MDMW Plate.

Figure 12:
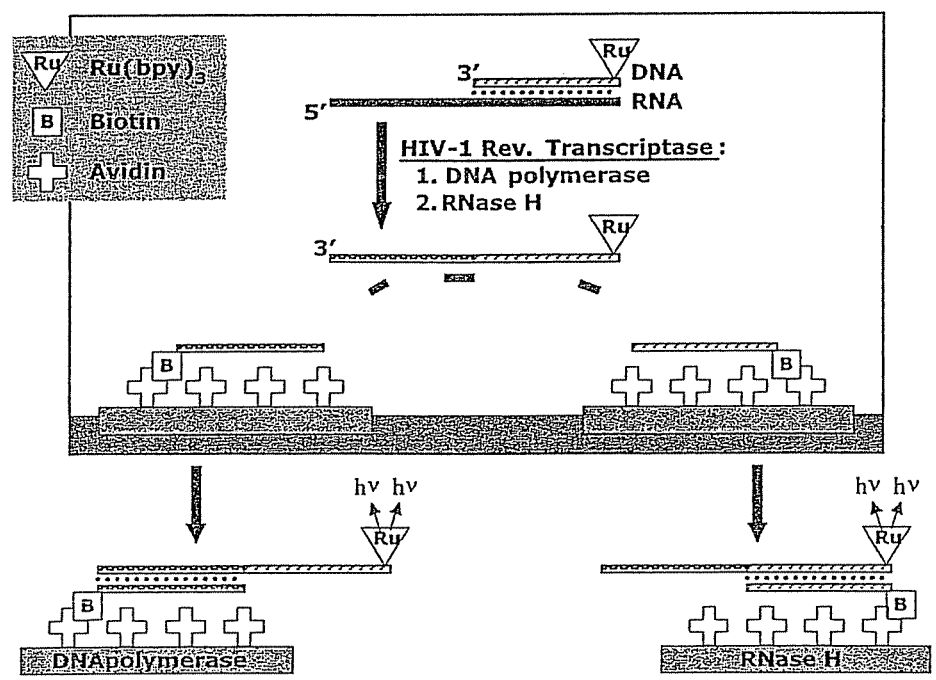
FIG. 12 is a schematic description of an assay for two activities of HIV RT enzyme.

The assay format is illustrated in FIG. 12. The enzyme substrate is a 5'-labeled (using TAG phosphoramidite, IGEN International, Inc.) DNA primer bound to the 3'-end of an RNA target sequence. The RDDP activity extends the DNA primer to make a complementary copy of the RNA sequence. The RNAse H activity selectively hydrolyzes RNA in RNA-DNA duplexes. RNAse activity is measured by hybridizing the labeled DNA product to an immobilized probe (3'-B13) that is complementary to the DNA primer sequence (thus measuring the RNAse catalyzed exposure of the DNA primer). The RDDP activity is measured by hybridizing the labeled DNA product to an immobilized probe (5'-B13) that is complementary to the extended DNA sequence (thus measuring the RDDP extension of the DNA primer).

The assay was conducted on a MDMW plate adapted for electrode induced chemiluminescence measurements and having four fluid containment regions exposed on the working electrode surface of each well (Plate C of Example 1). The two probes (3'-B13 and 5'-B13) were biotin-labeled to facilitate immobilization. Each probe was prebound to avidin. Assay domains were formed by immobilizing each probe in one fluid containment region of each well by microdispensing the avidin-probe complexes onto the fluid containment regions (between 100-1000 nL containing 1 pmol of probe) using a non-contact microdispensor (BioDot or Cartesian Technologies) and allowing the solutions to dry. The two additional fluid containment regions were used as control domains (one was coated with avidin, the other was not treated). The plates were blocked with a solution containing BSA and washed prior to use.

Figure 13A:
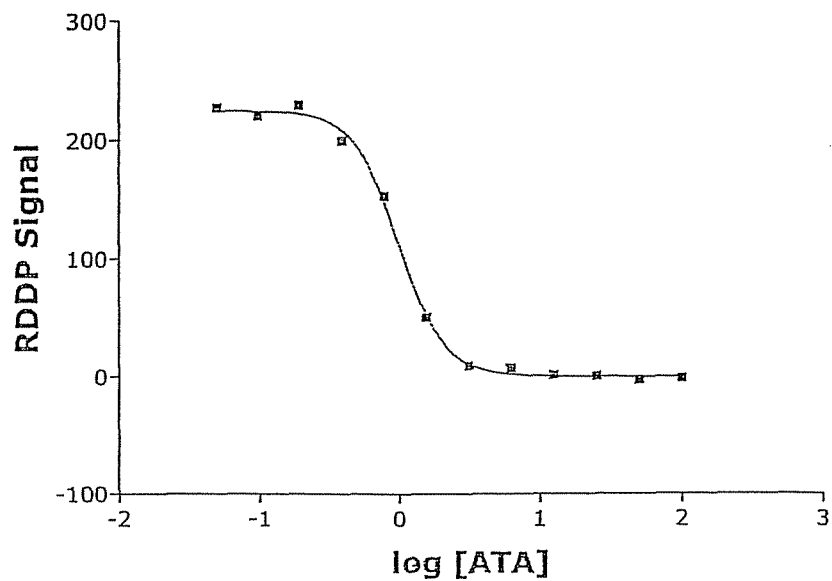
FIGS. 13A and 13B are graphical representations of the inhibition of two activities of HIV RT by an inhibitor.
Figure 13B:
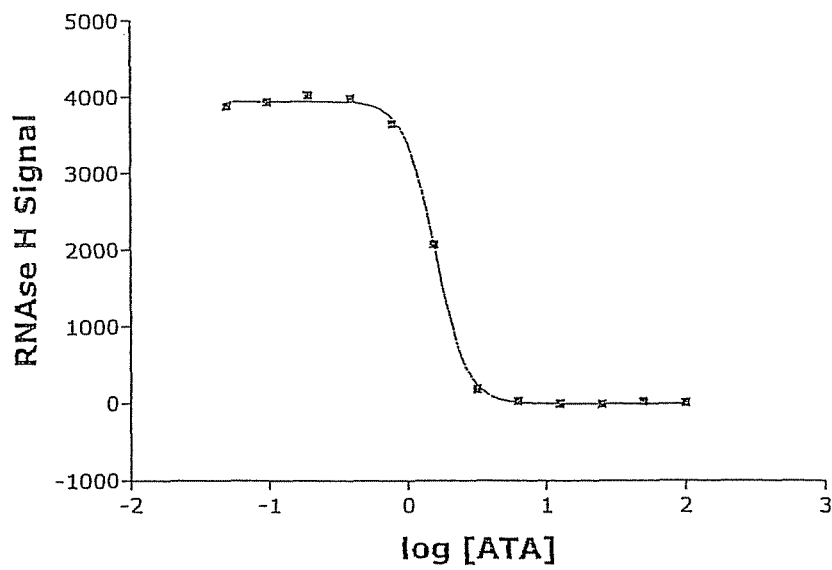

The assays were carried out by adding to the wells of plates 1 nmol of the dNTPs, 5 pmol of the substrate, 3 pmol of the enzyme and varying amounts of an RT inhibitor in 100 uL of a buffer containing 50 mM Tris ph 8.0, 40 mM KCl, 10 mM $MgCl_2$, 0.025% Triton® X-100, 2.5 mM DTT. The reaction mixture was incubated for 20 min at 22° C. and then quenched by the addition of EDTA. The plates were incubated for an additional 2 hours to allow the hybridization reactions to proceed. Tripropylamine was added (ORIGEN Assay Buffer, IGEN International and the products assayed by electrochemiluminescence measurements. The ECL signals were corrected by subtracting assay background (measured in wells in which EDTA was added prior to the enzyme). FIGS. 13A-B show that the inhibitor aurintricarboxylic acid (ATA; DuPont) inhibits both RNAse H (FIG. 13B) and RDDP activities (FIG. 13A). By contrast, 125 uM ddCTP (a chain terminating agent) completely inhibited the RDDP activity but had no effect on the RNAse H activity (data not shown).

Example 4

Detection of a Panel of Respiratory Disease Antigens

An MDMW plate adapted for ECL measurements and having 4 fluid containment regions on the working electrode surface exposed in each well (Plate C of Example 1) was coated with antibodies specific to four respiratory diseases: Influenza A, Influenza B, Respiratory Syncytial Virus (RSV), and *Streptococcus Pyogenes* (Strep A). Capture antibody solutions (50 ug/ml in phosphate buffered saline, PBS) were dispensed using a BioDot Dispenser onto the fluid containment regions within the wells (250 nl/spot) such that each well contained one assay domain coated with each antibody. The solutions were allowed to dry, at which time a 5% BSA solution was added (200 ul/well) and the plate refrigerated overnight. The plate was washed with PBS before use (4×250 ul/well).

Antigen solutions were prepared by diluting solutions of bacteria or purified virus obtained from commercial sources by 1000× or 100×, respectively, using PBS. The approximate titers after dilution were: $2.3 \times 10^{11}$ virus particles/ml Influenza A; 320 HA units/0.05 ml, or 0.1 mg/ml protein for Influenza B; $6.6 \times 10^8$ virus particles/ml RSV; $1.5 \times 10^4$ CFU/ml Strep A.

Figure 14:
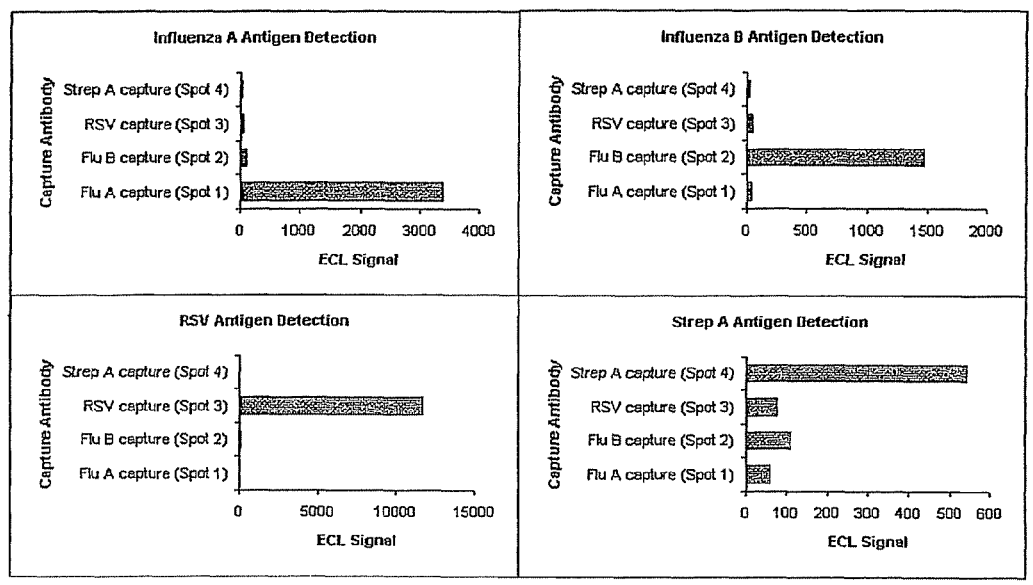
FIG. 14 is a graphical representation of the selectivity of a MDMW Plate designed to measure 4 different infectious agents.

To perform the assay, 100 ul of the diluted antigen solutions were combined with 450 ul of PBS containing 0.2% Tween-20. 75 ul of these solutions were combined with 10 ul of a solution of the appropriate labeled antibody solution (sulfonated derivative of $Ru(bpy)_3$) such that the final concentration was 3 ug/ml labeled antibody. 50 ul of this solution was added to individual wells of the washed plate and incubated for 8 minutes. The plate was then washed with PBS (4×200 ul/well) and 100 ul of ORIGEN Assay Buffer (IGEN International) was added to each well. The plate was then analyzed using electrochemiluminescence detection. FIG. 14 shows that each antigen was selectively measured in the appropriate assay domain.

Example 5

Measurement of Tyrosine Kinase and Serine/Threonine Kinase Activities in a Well of a MDMW Plate This example used an MDMW plate adapted for ECL measurements and having 4 fluid containment regions on the working electrode surface exposed in each well (Plate C of Example 1). Each fluid containment region received 250 nL of one of the following solutions: 1 mg/ml Poly-Glu:Tyr (4:1) (PGT) in PBS buffer with 0.0075% Triton; 1 mg/ml Myelin Basic Protein (MBP) in PBS buffer with 0.0075% Triton; 0.5 mg/ml Avidin in PBS buffer with 0.0075% Triton; 5% BSA solution in PBS. The plate was then dried overnight and blocked in a 5% BSA solution at 4° C. for 2 days. The plate was washed to remove blocking agent prior to use.

For phosphorylation of PGT (tyrosine kinase assay) 0.1 mU/µl of c-SRC was used, for phosphorylation of MBP (threonine kinase) 15 pg/µl of ERK-1 was used. The capture efficiency of the avidin-coated domain was determined by measuring the binding of bovine IgG labeled with biotin and a sulfonated form of $Ru(bpy)_3$.

Each spot (PGT, MBP, Avidin and BSA) was exposed to a solution of each enzyme/analyte (as well as to mixtures of the enzymes and analytes) in the presence of labeled (sulfonated derivative of $Ru(bpy)_3$) antibodies directed against the kinase products (anti-phosphotyrosine and anti-phospho-MBP (or, alternatively, using unlabeled primary antibodies and labeled secondary antibodies). After incubating the plates to allow the enzyme and binding reactions to proceed, a TPA-containing buffer was added and the plates were analyzed by ECL (no wash was required). Reported signals were corrected by subtracting background measured in the absence of enzyme/analyte. Each point includes an average of four measurements for background signal and 12 measurements for specific signal. The table in FIG. 15 summarizes results of this experiment.

The PGT domain only showed high signal in the presence of the tyrosine kinase src. As expected, the MPB gave high signal in the presence of the ERK-1, but also gave elevated signals in the presence of SRC, presumably because of the presence of several tyrosines in MPB and the relative non-specific nature of both SRC and the anti-phosphotyrosine antibody. The avidin domain gave a good signal in the presence of the biotinylated analyte and did not act as a substrate for the kinases. This result demonstrates the utility of including a binding domain, e.g., for capturing (and, optionally, purifying) kinases to be tested from crude samples. The BSA spot did not provide a significant signal in the presence of the analyte/enzymes and shows that the blocking agent did not show non-specific reactions with the assay reagents.

Example 6

Evaluation of the Detection Limits of MDMW Plates

In this Example, Applicants measured the detection limits of the ECL measurement of bovine IgG labeled with biotin and a sulfonated derivative of $Ru(bpy)_3$ (~2.3 labels per protein) as a function of the area of the binding domain. Binding domains were formed by coating Avidin onto one or more of the exposed regions (fluid containment regions) of the electrode (by microdispensing avidin solutions and drying on the surface of the electrode). Five plate types were prepared:
  Standard 96: Plate type B from Example 1 having a single large binding domain coated with avidin.
  4-Spot-1: Plate type C from Example 1 having 4 small fluid containment regions, three of which are coated with avidin to form a binding domain.
  4-Spot-3: Plate type C from Example 1 having 4 small fluid containment regions, only one of which is coated with avidin to form binding domains.
  7-Spot-1: Plate type D from Example 1 having 7 smaller fluid containment regions, three of which are coated with avidin to form a binding domain.
  7-Spot-3: Plate type D from Example 1 having 7 smaller fluid containment regions, only one of which is coated with avidin to form binding domains.

After standard blocking and washing procedures, a serial dilution of tag-IgG-biotin was assayed in 50 microliter volumes with 2 hour incubation time using intermittent shaking. The plates were read with a 2.5-4.5 volt scan for 5 seconds. FIG. 16 shows a log-log plot of the uncorrected data. Surprisingly, the detection limits are actually significantly better for the multi-array format than for the standard format. The relative detection limits (relative to the standard 96 plate) calculated for each plate type are: standard 96 (1.0), 4-spot-1 (4.2), 4-spot-3 (1.4), 7-spot-1 (4.4), 7-spot-3 (2.1). This is expected if most of the tag is captured at the working electrode spot. As the spot gets smaller, the total specific light emitted should stay constant, while the background signal decreases with area. On average for all calibrators above the detection limit, the signal for 1 of the 4 spots spotted is 2.7 times as high as the average signal when 3 spots are spotted. This indicates that most (~90%) of the tagged molecules are being captured on the single spot. This example demonstrates that assays in MDMW plates having small assay domains can have the same or better performance as assays in conventional single domain plates.

Example 7

Multi-Analyte Immunoassay of MDMW Plates

Sandwich immunoassays for four different cytokines—interleukin 1β(IL-1β), interleukin 6 (IL-6), interferon γ (IFN-γ) and tumor necrosis factor α (TNF-α)—were carried out simultaneously in the wells of plates manufactured according to the design and procedure described for Plate C in Example 1. Four capture antibodies (each selective for one of the analytes of interest) were patterned into distinct assay domains by microdispensing solutions of the antibodies on the fluid containment regions within each well (one antibody per region) and allowing the antibodies to adsorb to the surface of the working electrode. Solutions (0.25 uL) containing the antibody (at a concentration of 32 ug/mL for IL-1β and TNF-α or 64 ug/mL for IL-6 and IFN-γ) and 0.1% BSA in phosphate buffered saline were dispensed onto the fluid containment regions using a solenoid valve controlled microdispensor (Biodot Dispensor, Cartesian Technologies) and allowed to evaporate to dryness. The volume of the antibodies was sufficient to spread over all of the exposed electrode surface within a fluid containment region but was small enough so that the fluid did not spread past the boundary formed by the dielectric layer. After drying the antibody solution on the working electrode, the plate tops were attached and the excess unbound antibody was removed (and uncoated surfaces blocked) by filling the wells with a solution containing 5% (w/v) bovine serum albumin (BSA) in phosphate buffered saline (PBS). The plates were incubated with the blocking solution overnight at 4° C. and then washed with PBS.

The assays were carried out by the steps of i) adding 0.02 mL of the sample to the well and incubating for 1 hour on a plate shaker; ii) washing the wells with PBS; iii) adding 0.02 mL of a solution containing 2,000 ng/mL each of four detection antibodies (labeled with NHS ester 1) against the four analytes of interest and incubating for 1 hour on a plate shaker; iv) washing with PBS; v) introducing 0.1 mL of a solution containing tripropylamine in phosphate buffer (ORIGEN Assay Buffer, IGEN International) and vi) measuring ECL. FIGS. 17A-17D demonstrate that each of the analytes of interest can be independently measured in a single sample in a single well of a multi-well assay plate. The figures show ECL emitted from each assay domain as a function of the concentration of each analyte. The introduction of a specific analyte led to a linear increase in ECL with analyte concentration (relative to the background signal measured in the absence of any analyte) at assay domains having capture antibodies directed against that analyte, but did not affect the ECL at assay domains having antibodies directed against the other analytes. FIG. 18 shows a CCD image of the ECL emitted from a sector of wells used to assay solutions containing mixtures of the four analytes. The highlighted well is annotated to show the arrangement of the four assay domains. That specific well was used to assay a sample having 250 pg/mL each of IL-1β and TNF-α and 8 pg/mL each of IL-6 and IFN-γ.

Example 8

Multi-Plex Assay for Total EGF Receptor and Auto-Phosphorylated EGF Receptor This example shows an ECL assay that measures in one well of a MDMW Plate total (phosphorylated and non-phosphorylated) EGF Receptor (T-EGFR) and phosphorylated EGF Receptor (P-EGFR).

Preparation of Lysates for Multi-Plex:

1. A-431 cells were cultured in 150 mm tissue culture dishes and serum starved overnight (DMEM supplemented with 1% Penicillin-Streptomycin and 1% Sodium Pyruvate).
2. Following two rinses with serum-free media, one dish was stimulated with 200 nM EGF in serum-free media for 15 minutes at room temperature. The unstimulated plate was given serum-free media only.
3. The cells were rinsed with two volumes of PBS.
4. 2 mls of a modified RIPA buffer (fresh sodium orthovanadate added the morning of the assay) was added to the dishes. RIPA buffer included: 1 mM neat sodium orthovanadate, 150 mM NaCl, 50 mM Tris, 6 mM Deoxycholate, 0.5% NP40, in water with a fresh protease inhibitor tablet, 1 tablet per 10 mL buffer). Cells were incubated with the RIPA for 10 minutes on ice.
5. Supernatant was collected and quantitated using the Pierce BCA Protein Assay.

Protocol for Multiplex Assay:

1. Biotin-labeled antibodies for T-EGFR (specific for the cytoplasmic domain of EGFR) and P-EGFR (anti-phosphotyrosine) were prebound (1 hour) with one equivalent of avidin and deposited by microdispensing (one antibody per region, 0.5 pmol per region in 0.25 uL) onto two of the four fluid containment regions in each well of a MDMW Plate (Plate C of Example 1). The two remaining fluid containment regions were used as controls for non-specific binding and cross-reactions. One region was coated with Avidin only. The other was left bare but eventually blocked with BSA.
2. The antibodies were allowed to dry. The wells were then blocked for one hour at room temperature with 200 µl per well of 5% BSA in water.
3. The plates were washed four times with dH$_2$O.
4. 50 µg/well of lysate was added to each well of the 96 well plates and shaken intermittently for one hour.
5. The plates were washed four times with dH$_2$O.
6. The Sulfo-Tag™-labeled α-EGFR antibody (50 uL of 33 nM) was added and the binding reaction allowed to proceed for 1 hour at room temperature with shaking. The plates were washed four times with dH$_2$O.
7. 100 µl per well of 100 mM TPA with 400 mM gly-gly assay buffer was added just prior to ECL analysis.
8. The plates were analyzed using ECL detection.

The table below compares the ECL signals measured from the T-EGFR and P-EGFR assays for lysates from stimulated and unstimulated cells. As expected, over the time course of the experiment, the levels of T-EGFR do not change considerably on stimulation, however, a large increase in P-EGFR was observed.

|  | Analyte | |
| --- | --- | --- |
| Sample | T-EGFR | P-EGFR |
| Unstimulated | 24,200 | 57 |
| Stimulated | 23,545 | 122 |

Example 9

Multi-Plex Assay for Detection of Autophosphorylated and Nonphosphorylated EGF Receptor This example shows an ECL assay that measures both nonphosphorylated EGF receptor and EGF receptor that is phosphorylated at tyrosine 1173 in a single well of a MDMW Plate.

A-431 cell lysates were prepared as described in Example 8, except that separate dishes of cells were stimulated with 0.2 nM, 5 nM and 200 nM EGF.

Protocol for Multiplex Assay:

1. Antibodies specific for EGF receptor that is autophosphorylated at tyrosine 1173 (pY1173) and antibodies specific for EGF receptor that is not phosphorylated at tyrosine 1173 (Y1173) were deposited by microdispensing (one antibody per region, 0.2 pmol per region in 0.25 uL) and passively adsorbed onto two of the four fluid containment regions in each well of a MDMW Plate (Plate C of Example 1). The two remaining fluid containment regions were used as controls for non-specific binding and cross-reactions; these regions were left bare but eventually blocked with BSA.
2. The antibodies were allowed to dry overnight. The wells were then blocked for one hour at room temperature with 200 µl per well of 5% BSA in water.
3. The plates were washed with PBS.
4. 5 µg/well of lysate was added to each well of the 96 well plates and the plates were shaken intermittently for three hours.
5. The plates were washed with PBS.
6. A Sulfo-TAG label labeled α-EGFR antibody directed against the extracellular domain of the receptor (50 uL of a 33 nM solution) was added and the binding reaction allowed to proceed for 1 hour at room temperature with shaking. The plates were washed four cycles with PBS.
7. 150 µl per well of 100 mM TPA with 400 mM gly-gly assay buffer was added just prior to ECL analysis.
8. The plates were analyzed using ECL detection in a Sector HTS™ plate reader (Meso Scale Discovery).

FIGS. 19A-D demonstrate that the amount of autophosphorylation of the tyrosine at position 1173 on the EGF receptor can be controlled and quantified in a single well of a multi-well assay plate. The schematic in FIG. 19A shows placement of the pY1173 and Y1173 antibodies on two diagonally opposed fluid containment regions in the same well. The EGF receptor contained in A-431 cell lysates binds to the appropriate surface immobilized antibody. Specifically, only the phosphorylated tyrosine at position 1173 binds the pY1173 antibody, and only the nonphosphorylated tyrosine at position 1173 binds to the Y1173 antibody. Competition for binding of the receptor to more than one assay domain in a single well is circumvented in this format. The reporter α-EGFR antibody binds the extracellular domain of both receptors. The CCD images in FIGS. 19B-D show ECL emitted from each assay domain as a function of increasing EGF concentration. No detectable autophosphorylation of tyrosine 1173 was observed at 0.2 nM EGF, approximately 50% of the receptor was phosphorylated at 5 nM EGF, and approximately 90% was phosphorylated at 200 nM EGF.

Example 10

Measurement of Tyrosine Kinase and Serine/Threonine Kinase Activities in a Well of a MDMW Plate This example used an MDMW plate adapted for ECL measurements and having 4 fluid containment regions on the working electrode surface exposed in each well (Plate C of Example 1). Each of the four fluid containment regions received 250 nL of one of the four following solutions: (i) 0.5 mg/ml Poly-Glu:Tyr (4:1) (PGT) in PBS buffer with 0.015% Triton; (ii) 0.2 mg/ml Myelin Basic Protein (MBP) in PBS buffer with 0.015% Triton; (iii) 0.3 mg/ml Streptavidin in PBS buffer with 0.015% Triton; (iv) 0.3 mg/ml BSA solution in PBS with 0.15% Triton. The plate was then dried for 1-1.5 hours at ambient conditions, vigorously washed with PBS containing 0.1% Triton, washed with water and blocked in a 5% BSA solution for at least 2 hours at room temperature. The washing included a bottom wash using a 96-well Plate Washer from Biotech that allows the creation of a constant flow of wash solution in the well and was very efficient for washing out an excess of peptides/proteins from the electrode surface. The washing with the Triton-containing solution was followed by 3× washes to remove traces of Triton. After blocking, the plate was washed again to remove blocking agent prior to use.

For phosphorylation of PGT (tyrosine kinase assay), 0.05 mU/μl of c-SRC was used; for phosphorylation of MBP (threonine kinase), 2 nM of ERK-2 was used. The capture efficiency of the Streptavidin-coated domain was determined by measuring the binding of bovine IgG labeled with biotin and a sulfonated form of Ru(bpy)$_3$ (Sulfo-TAG™ label by Meso Scale Discovery).

Each spot (PGT, MBP, Streptavidin and BSA) was exposed to a solution of unlabeled primary antibodies directed against phosphotyrosine and phosphorylated MBP and labeled secondary antibodies. After incubating the plates to allow the enzyme and binding reactions to proceed, a TPA-containing buffer was added and the plates were analyzed by ECL (no wash was required). Each point includes an average of 12 measurements with CV's of 7-10%. Table A below summarizes the results obtained from this experiment.

TABLE A

| Domain | No Enzyme/ No blgG* | Analyte blgG* Only | SRC-only | ERK2-only |
|---|---|---|---|---|
| SA | 272 | 5,447 | 324 | 309 |
| PGT | 990 | 953 | 17,223 | 1,153 |
| MBP | 1,241 | 1,354 | 1,237 | 32,810 |
| BSA | 138 | 134 | 168 | 209 |

The PGT and MBP domains only showed high signal in the presence of the tyrosine kinase SRC and Threonine kinase (ERK2), respectively. Titration curves of the activity of both kinases (SRC and ERK) exhibited nearly linear response on corresponding domains. The Streptavidin domain gave a good signal in the presence of the biotinylated analyte and did not act as a substrate for the kinases. This result demonstrates the utility of including a binding domain, e.g., for capturing (and, optionally, purifying) kinases to be tested from crude samples. The BSA spot did not provide a significant signal in the presence of the analyte/enzymes and shows that the blocking agent did not show non-specific reactions with the assay reagents.

7. INCORPORATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A multi-well plate comprising a plate top having plate top openings and a plate bottom mated to said plate top to define a plurality of wells of said multi-well plate, said plurality of wells comprising a plurality of assay domains, said plate bottom comprising a substrate having a top surface with electrodes patterned thereon and a bottom surface with electrical contacts patterned thereon, said contacts being positioned on said bottom surface between said wells of said plate, wherein the top and bottom surfaces are aligned and stacked relative to one another in the substrate,
   wherein said electrodes and contacts are patterned into individually addressable sectors of wells, each well comprises:
   (a) a working electrode on said top surface of said substrate, wherein said working electrode is electrically connected to a first of said electrical contacts; and
   (b) a counter electrode on said top surface of said substrate, wherein said counter electrode is electrically connected with a second of said electrical contacts and said working and counter electrodes are electrically isolated,
   wherein said plurality of assay domains comprises: (i) one or more assay domains comprising one or more binding reagents capable of binding one or more analytes in a sample, and one or more additional domains comprising (ii) a first control domain comprising a control binding reagent capable of binding a control analyte added to said sample, (iii) a second control domain comprising a blocking agent; or (iv) combinations thereof.

2. The multi-well plate of claim 1, wherein said first control domain controls for one or more of the following: (i) non-specific binding or biochemical activity; (ii) chemical interference with ECL generation; (iii) optical interference with light transmission; (iv) pipetting errors; (v) timing errors; (vi) variations in mixing; (vii) variations in temperature; and (viii) assay module variation.

3. The multi-well plate of claim 1, wherein said second control domain controls for non-specific binding.

4. The multi-well plate of claim 1, comprising additional domains (ii) and (iii).

5. The multi-well plate of claim 1, wherein said assay module is configured to detect said one or more analytes and said control analyte in a sandwich immunoassay format.

6. The multi-well plate of claim 5, wherein the blocking reagent is a control antibody not paired with a detection antibody used in said assay.

* * * * *